United States Patent [19]
Kanebako et al.

[11] Patent Number: 5,680,471
[45] Date of Patent: Oct. 21, 1997

[54] IMAGE PROCESSING APPARATUS AND METHOD

[75] Inventors: Toyomitsu Kanebako, Tochigi-ken; Hiroshi Nakayama, Ootawara, both of Japan

[73] Assignee: Kabushiki Kaisha Toshiba, Kawasaki, Japan

[21] Appl. No.: 281,037

[22] Filed: Jul. 27, 1994

[30] Foreign Application Priority Data

Jul. 27, 1993 [JP] Japan ................................. 5-184857
Jul. 30, 1993 [JP] Japan ................................. 5-189886

[51] Int. Cl.⁶ ........................................................ G06K 9/00
[52] U.S. Cl. .................. 382/128; 382/132; 382/190; 364/413.23; 128/653.2
[58] Field of Search ........................ 382/128, 132, 382/173, 190; 128/661.08, 661.1, 774, 653.2; 364/413.23

[56] References Cited

U.S. PATENT DOCUMENTS

| | | | |
|---|---|---|---|
| 4,101,961 | 7/1978 | Reiber | 382/132 |
| 4,692,864 | 9/1987 | Shimoni et al. | 364/413.23 |
| 4,771,792 | 9/1988 | Seale | 128/774 |
| 5,072,384 | 12/1991 | Doi et al. | 382/173 |
| 5,107,838 | 4/1992 | Yamaguchi | 128/653.2 |
| 5,139,020 | 8/1992 | Koestner et al. | 128/661.1 |
| 5,188,106 | 2/1993 | Nappholz et al. | 128/661.08 |
| 5,239,591 | 8/1993 | Ranganath | 382/128 |
| 5,274,549 | 12/1993 | Almasi | 382/128 |
| 5,377,279 | 12/1994 | Hanafusa et al. | 382/141 |
| 5,457,754 | 10/1995 | Han et al. | 382/128 |

OTHER PUBLICATIONS

A. Ohhashi, et al.; "Semi–Automatic Drawing of ROI on Medical Image –The First Stage", Med. Imag. Tech.; vol. 9, No. 2, Jun. 1991; pp. 153–161.

*Primary Examiner*—Jose L. Couso
*Assistant Examiner*—Anh Hong Do
*Attorney, Agent, or Firm*—Oblon, Spivak, McClelland, Maier & Neustadt, P.C.

[57] ABSTRACT

An image processor acquires an image including a desired portion of an object to be examined. An image memory temporarily stores the acquired image, and an outline is extracted from an area of interest from the desired portion of the object. The outline is extracted by dividing the image stored in the image memory into plural areas using parallel lines, and a threshold value is set for each of the plural divided areas. Points having values exceeding the threshold values are connected.

12 Claims, 28 Drawing Sheets

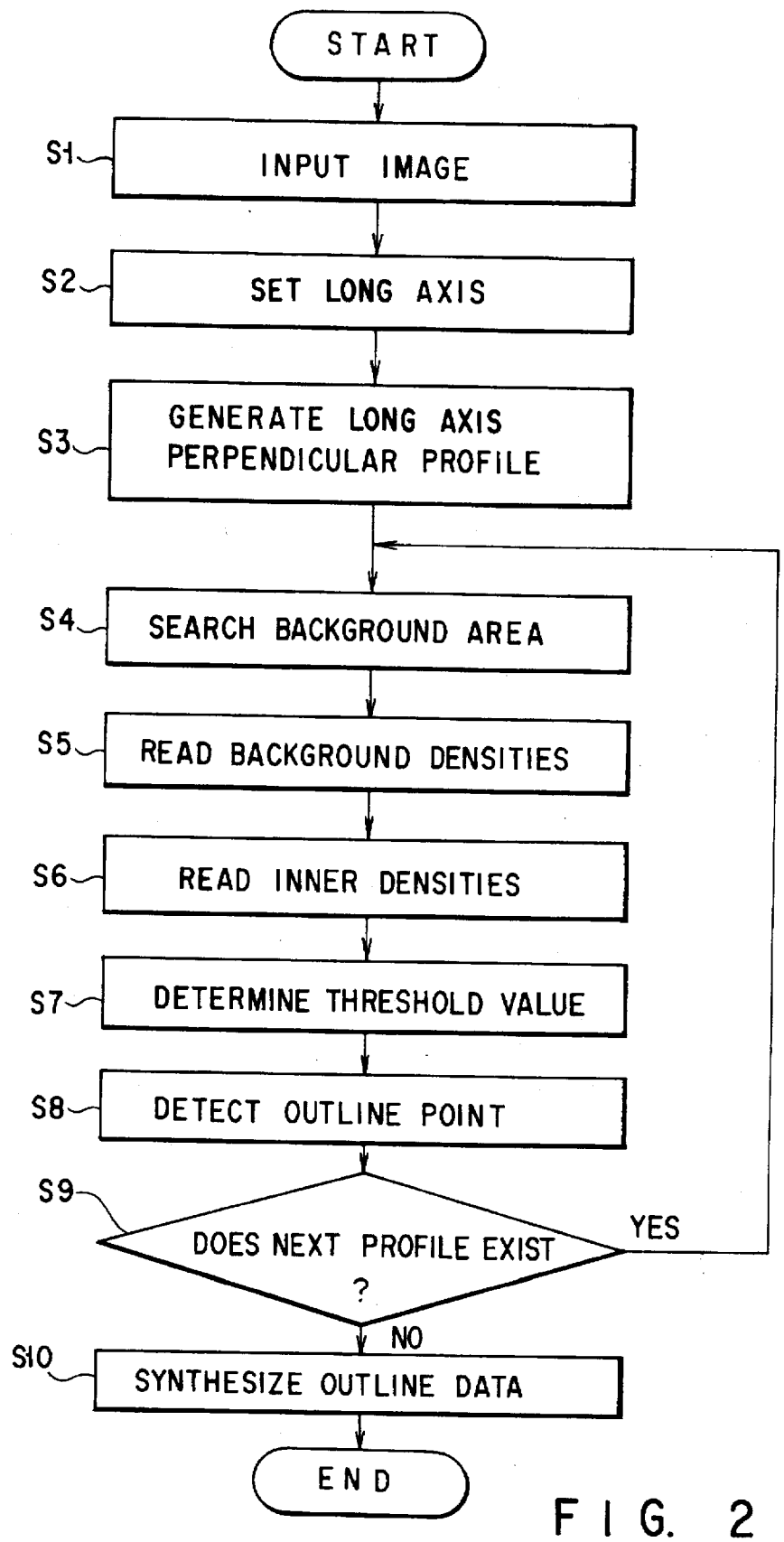
F I G. 2

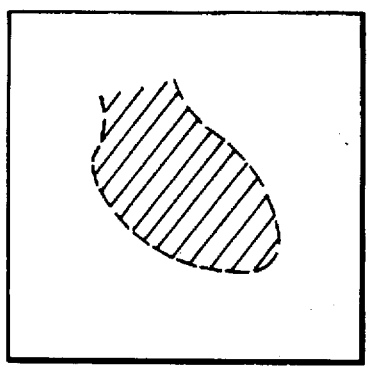
⬚ LEFT VENTRICLE
F I G. 3A
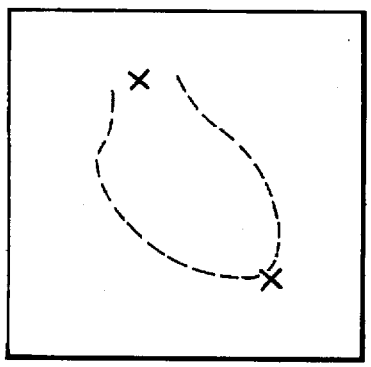
X : INSTRUCTION POINT
F I G. 3B
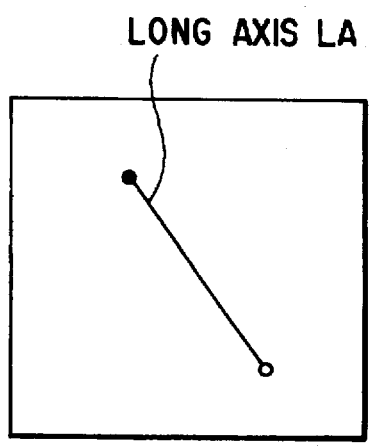
● : MIDDLE POINT OF AORTIC VALVE
○ : APEX PORTION OF HEART
F I G. 3C

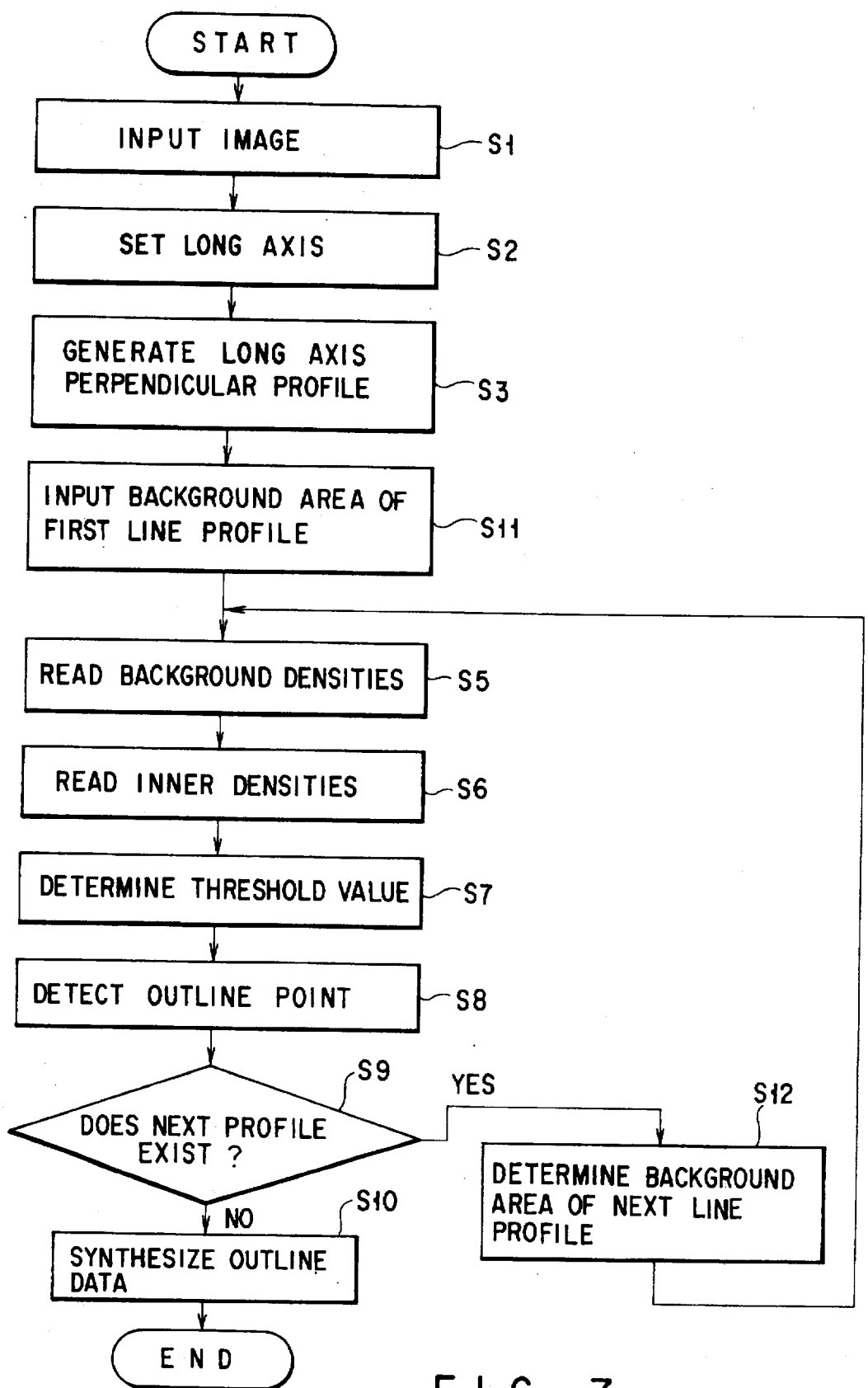
F I G. 7

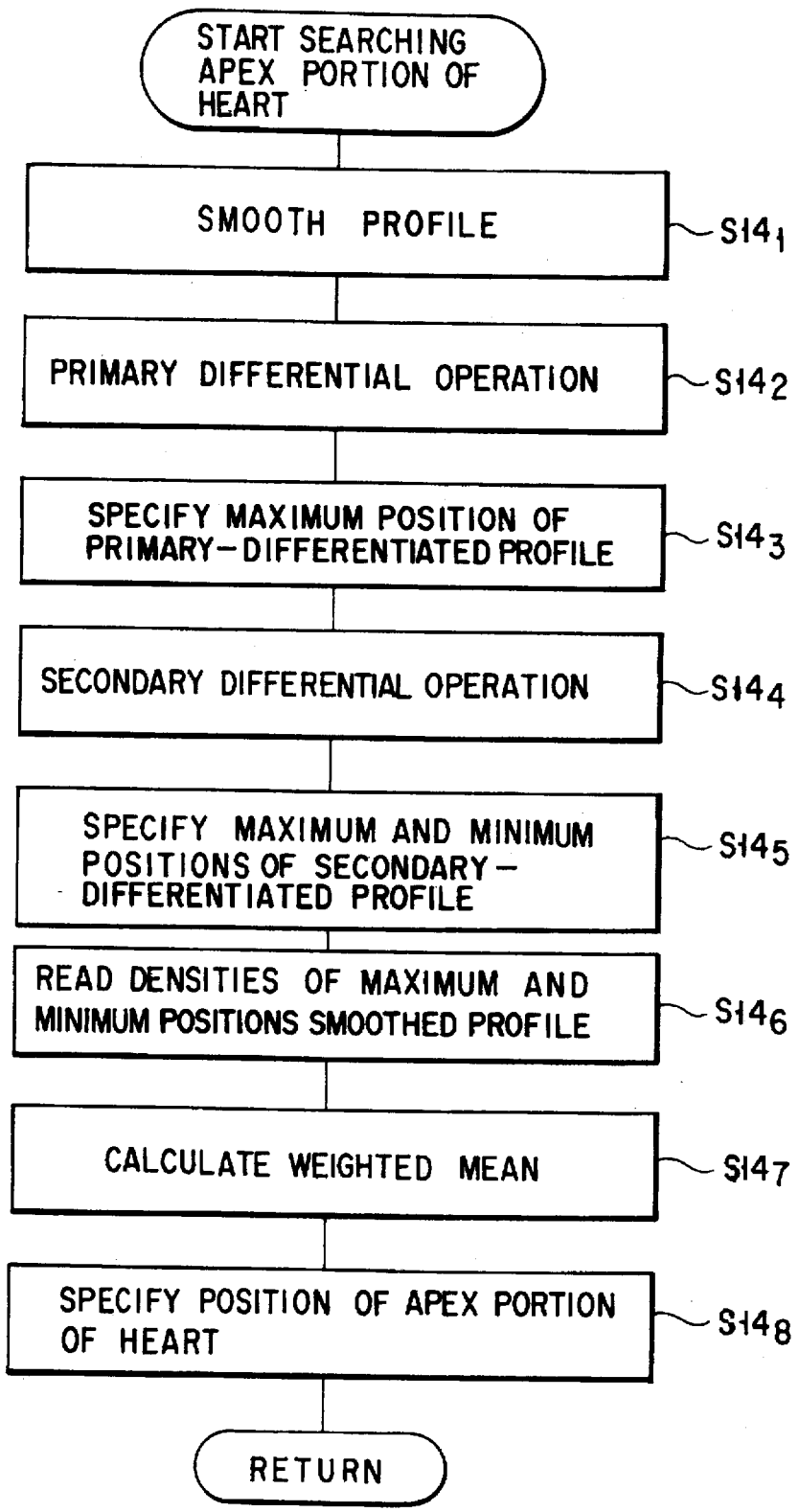
F I G. 19

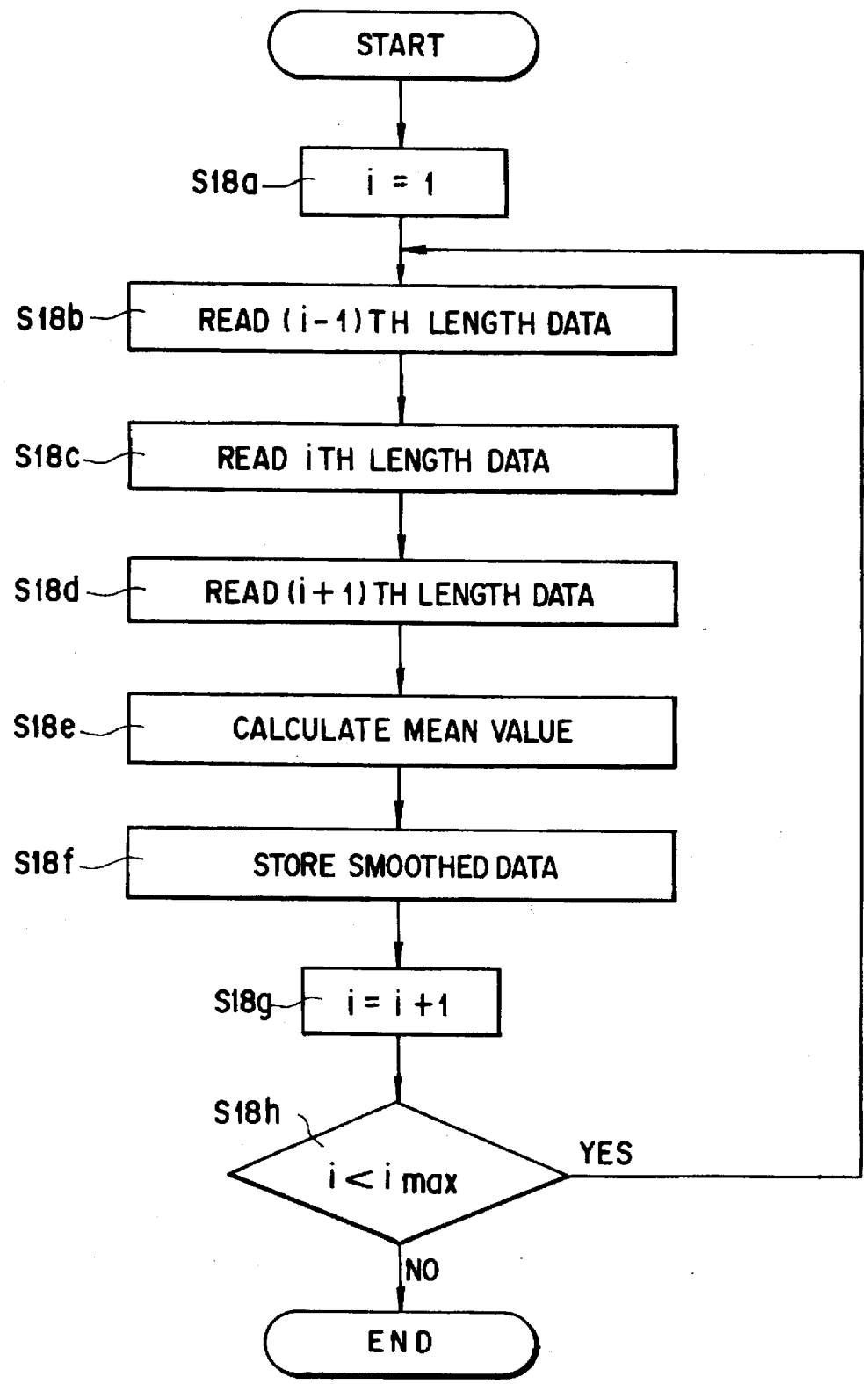
F I G. 23

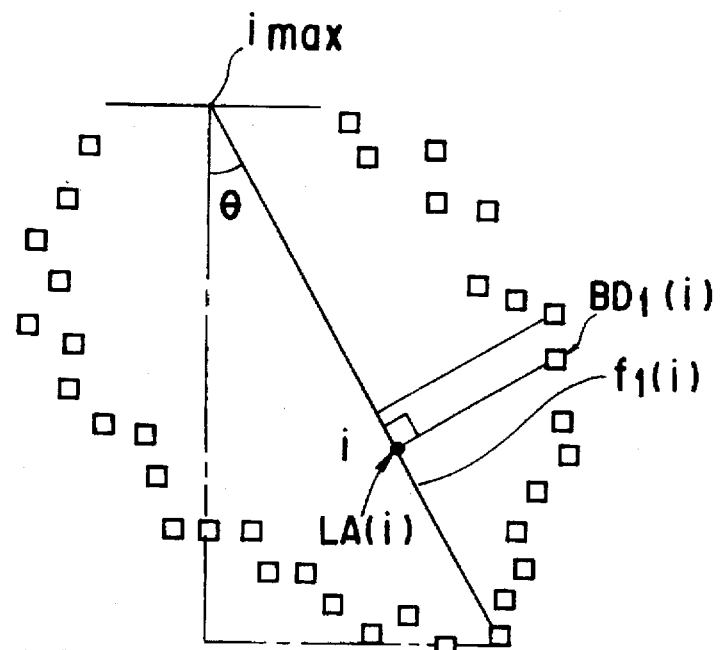
FIG. 24A
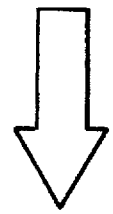
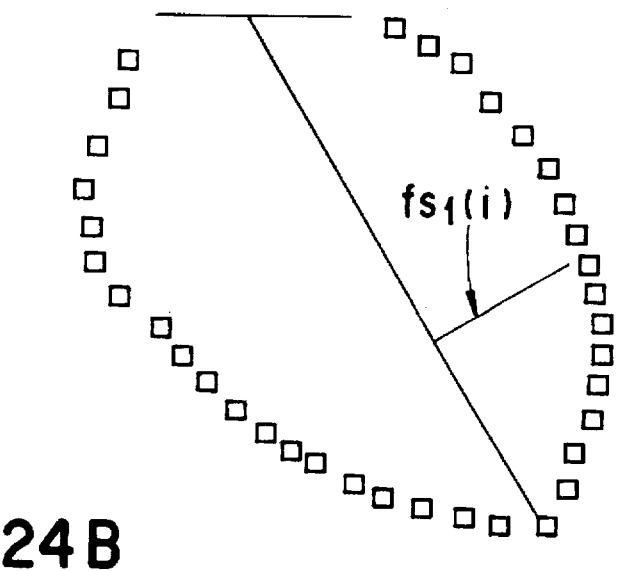
FIG. 24B

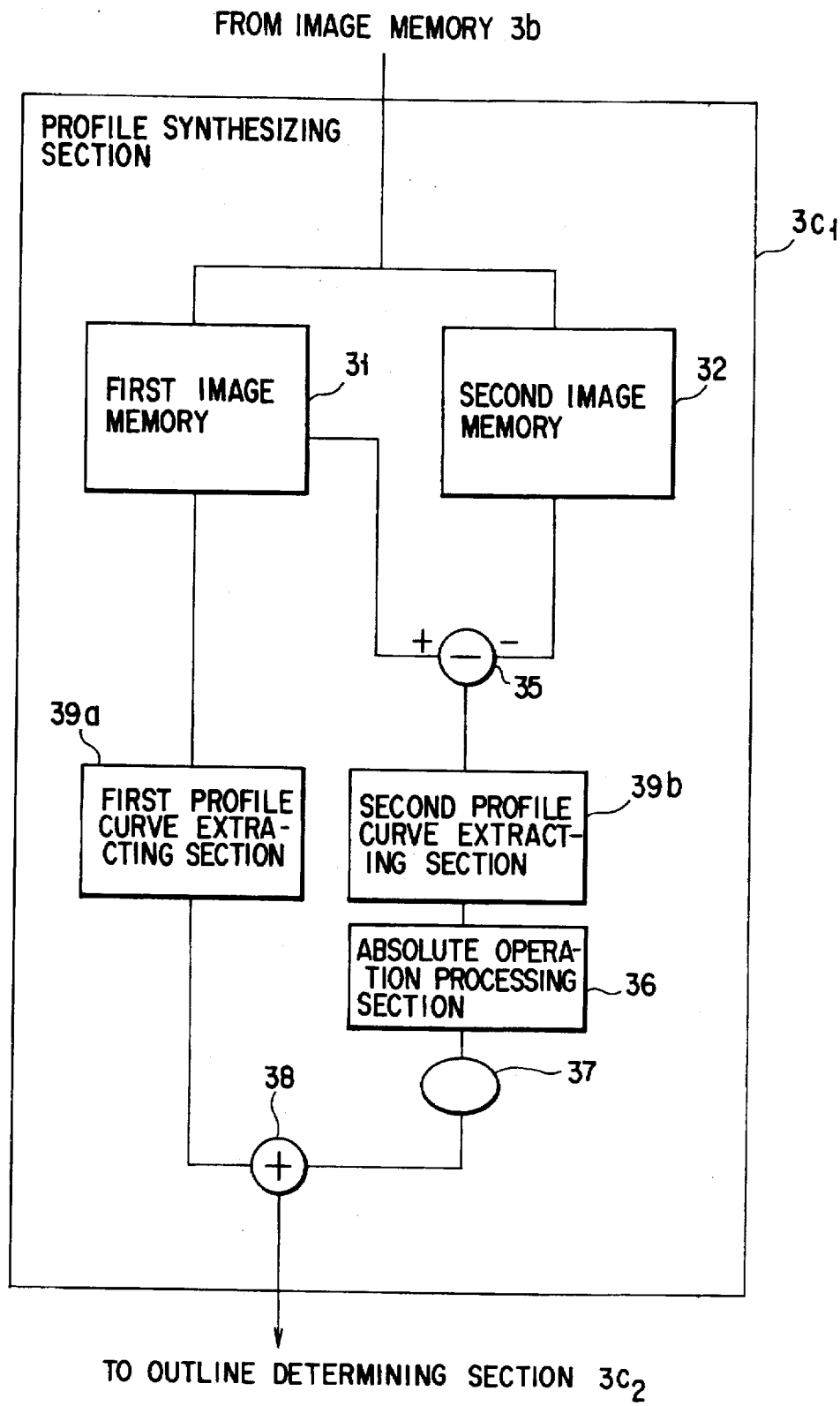
F I G. 30

1

IMAGE PROCESSING APPARATUS AND METHOD

BACKGROUND OF THE INVENTION

1. Field of the Invention

The present invention relates to an image processing apparatus and method of drawing an area of interest (e.g., the outline of a portion of interest, e.g., the left ventricle of the heart, of an image in function analysis of the left ventricle of the heart) of an image on the basis of pixel value (density) data.

2. Description of the Related Art

When an X-ray image obtained by photographing and fluoroscopically observing an object to be examined upon injection of a contrast medium into the living body is to be used for medical treatment, image processing for extracting an area of interest of the image is often performed. As such an image processing method, a left ventricle outline extracting method is available, in which, for example, the outline of the photographed left ventricle portion of the heart is extracted from a left ventricle contrast medium image.

The left ventricle outline extracting method is performed as follows.

An operator sets a certain threshold value, and checks whether the pixel value (density) of each pixel is larger (or smaller) than the threshold value. An area in which the pixel values are larger (or smaller) than the threshold value is considered as the left ventricle of the heart, and the boundary of the area is drawn as the outline of the left ventricle of the heart.

In the above conventional method, the following problems are posed.

First, in an image in which variations and gradients of the densities of a background (i.e., a portion other than a desired area) are larger than those of a contrast medium, if a threshold value is set to detect the entire desired area, an area other than the desired area is also detected. In contrast to this, if a threshold value is set such that an area other than a desired area is not detected at all, part of the desired area may not be detected. As a result, the outline of the desired area cannot be extracted.

Second, in photographing and fluoroscopically observing an object to examined to obtain, e.g., a left ventricle contrast medium image, X-ray radiation cannot always be performed at the optimal positioning, and a structural object such as the rib may appear near the left ventricle of the heart in the image. If threshold value processing is applied to an image having such a structural object appearing therein to extract the outline of the left ventricle of the heart, various difficulties are posed.

The pixel values of a structure object portion are as small as those of the left ventricle of the heart. For this reason, if one threshold value set to discriminate the left ventricle of the heart is used to discriminate the pixel value data of the entire image, detection errors are frequently caused. For example, even an area of the structural object is erroneously recognized as an area of the left ventricle of the heart. As a result, the extraction precision greatly deteriorates.

In order to prevent the deterioration in extraction precision, a proper threshold value may be selected for each portion in an image to prevent erroneous detection of a structural object. However, in the method of selecting a threshold value for each portion, the labor required for the operation greatly increases. As a result, the burden of operation on the operator increases, and the efficiency of outline extraction processing deteriorates.

Third, in an image at the end of diastole, an area in which the concentration of a contrast medium is low tends to be produced near the left ventricle of the heart because blood having no contrast medium mixed therewith flows from the left ventricle of the heart. In this portion, it is difficult to determine a threshold value smaller than the density value of a structural object such as the rib outside the ventricle of the heart and larger than the density value of the left ventricle of the heart. For this reason, a portion in which the concentration of the contrast medium is low is erroneously recognized as a portion outside the ventricle of the heart.

SUMMARY OF THE INVENTION

It is an object of the present invention to provide an improved image processing apparatus and method. More specifically, the apparatus and method are capable of:

(1) extracting the outline of a desired area even if variations and gradients of the densities of a background (i.e., a portion other than the desired area) are larger than those of the densities of the desired area, (2) extracting the outline of a desired object or of an area of interest thereof, even in an image in which a structural object other than the object appears, with high precision and high operation efficiency without being influenced by the pixel value data of the structural object, and (3) accurately recognizing a desired area even if the density of the desired area (e.g., the concentration of a contrast medium) greatly varies.

The first aspect of an image processing apparatus according the present invention is characterized by comprising: image acquiring means for acquiring an image including a desired portion of an object to be examined; image memory means for temporarily storing the acquired image; and outline extracting means for extracting an area of interest from the desired portion of the object, wherein the outline extracting means includes means for dividing the image stored in the image memory means into a plurality of areas by using parallel lines, means for setting a threshold value for each of the plurality of divided areas, and means for connecting points having values exceeding the threshold values. The outline extracting means further includes long axis setting means for setting a long axis in a first direction of the image, first profile generating means for drawing a plurality of perpendicular lines on the image in a second direction perpendicular to the long axis, and generating a plurality of first profile data for the respective perpendicular lines, density setting means for searching a background area outside the area of interest and an inner area inside the area of interest on the basis of the first profile data, and obtaining densities of the background area and the inner area, threshold value determining means for determining a threshold value on the basis of a weighted mean of the densities of the background area and the inner area, and outline setting means for determining an outline points constituting a boundary between the outside and inside of the area of interest by using the threshold values determined for the respective first profile data, and connecting the outline points.

The first aspect of an image processing method according the present invention is characterized by comprising: the first step of acquiring an image including a desired portion of an object to be examined; the second step of temporarily storing the acquired image; and the third step of extracting an area of interest from the desired portion of the object, wherein the third step includes the substeps of dividing the image stored in the image memory means into a plurality of areas by using parallel lines, setting a threshold value for each of the plurality of divided areas, and connecting points exceeding the threshold values. The third step further includes the substeps of setting a long axis in a first direction of the image, drawing a plurality of perpendicular lines on the image in a second direction perpendicular to the long axis, and generating a plurality of first profile data for the respective perpendicular lines, searching a background area outside the area of interest and an inner area inside the area of interest on the basis of each of the first profile data, and obtaining densities of the background area and the inner area, determining a threshold value on the basis of weighted mean of the densities of the background area and the inner area, and determining outline points constituting a boundary between the outside and inside of the area of interest by using the threshold values determined for the respective first profile data, and connecting the outline points.

According to the first aspect of the present invention, an image is divided into a plurality of areas on parallel lines, and a threshold value suitable for each area is determined. An outline is determined on the basis of these threshold values. Therefore, a desired outline can be extracted even if variations and gradients of the densities of a background (a portion other than the desired area) are larger than those of the densities of a contrast medium image portion as the desired area.

The outline extracting means further includes means for searching a background area on the first profile data.

As described above, even with regard to an image with a background having an gradient, e.g., a left ventricle contrast image, a desired outline of the left ventricle of the heart can be extracted.

The first profile generating means includes means for drawing the plurality of perpendicular lines at substantially equal intervals, and search starting point setting means for setting a representative point of the background area as a search starting point at a predetermined position spaced apart by a predetermined distance from an outline point obtained from the immediately preceding first profile data.

The first profile generating step includes the substeps of detecting a maximum density position in the first profile data between the predetermined position on the outside and the long axis, in a direction from the predetermined position on the outside to the long axis, and replacing the maximum density position detected by the position detecting means with a background area density.

As described above, even with regard to a contrast image in which a left ventricle portion overlaps an nonuniform background tissue portion, a desired outline of the left ventricle of the heart can be extracted.

As described above, according to the first aspect of the present invention, even if variations and gradients of the densities of a background (i.e., a portion other than a desired area) are larger than those of the densities of a contrast medium image portion as the desired area, the outline of the desired area can be extracted.

The second aspect of an image processing apparatus according the present invention is, in the first aspect, characterized in that the first profile generating means includes position detecting means for detecting a maximum density position in the first profile data between the predetermined position on the outside and the long axis, in a direction from the predetermined position on the outside to the long axis, and background area density replacing means for replacing the maximum density position detected by the position detecting means with a background area density. The outline extracting means further includes second data generating means for generating second profile data representing a density distribution at a plurality of pixel positions on the long axis, and area-of-interest end determining means for automatically determining one end of the area of interest on the long axis on the basis of the first profile data and a position near the boundary of the area of interest. The outline setting means further includes distance data generating means for obtaining a perpendicular distance to the long axis on the basis of the outline point determined for each of the first profile data, and outline smoothing means for replacing the perpendicular distance obtained by the distance data generating means with an mean value of a sum of perpendicular distances obtained on the basis of outline points of at least adjacent first profile data. The area of interest of the object is the left ventricle of the heart, and the long axis is a line segment connecting a position near an apex portion of the left ventricle of the heart and a middle point of the aortic valve. The first data generating means includes means for generating first profile data using a position near the apex portion of the heart as a starting point, and the outline setting means includes means for detecting an outline point of each of the first profile data in the first direction away from the apex portion of the heart toward the aortic valve. The area-of-interest end determining means includes differentiation means for performing differentiation of the second profile data twice, means for specifying maximum and minimum values after the differentiation is performed twice, and means for calculating a weighted mean of the second profile data in both positions of the maximum and minimum values, and specifying a position, on the long axis, which corresponds the obtained result as a position of the apex portion of the heart. The background density replacing means includes determination means for determining whether the maximum density position is between an outline point set by the immediately preceding first profile data and the predetermined position on the outside, and means for replacing the background density with a density of the maximum density position on the basis of the determination result obtained by the determination means. The background density replacing means includes determination means for determining whether the maximum density position is between an outline point set by the immediately preceding first profile data and the predetermined position on the outside, and starting point changing means for changing the search starting point to the maximum density position on the basis of the determination result obtained by the determination means.

The second aspect of an image processing method according the present invention is, in the first aspect, characterized in that the third step further includes the substeps of obtaining a perpendicular distance to the long axis on the basis of the outline point determined for each of the first profile data, and replacing the perpendicular distance obtained by the distance data generating means with an mean value of a sum of perpendicular distances obtained on the basis of outline points of at least adjacent first profile data.

Further, in the first and second aspects of the present invention, the density setting means includes means for setting an average of a sum of currently read background densities of the first profile data and previously read background densities of the first profile data. The first profile generating means includes means for generating first profile data proportional in number to a length of the long axis. The search starting point determining means includes means for setting a point spaced apart outward from the outline point by a distance proportional to a length of the long axis as a search starting point. The outline setting means further includes distance data generating means for obtaining a perpendicular distance to the long axis on the basis of an outline point determined for each of the first profile data, and outline smoothing means for replacing the perpendicular distance obtained by the distance data generating means with an mean value of a sum of perpendicular distances obtained on the basis of outline points of at least adjacent first profile data. The area of interest of the object is the left ventricle of the heart along the long axis is a line segment connecting a position near an apex portion of the left ventricle of the heart and a middle point of the aortic valve. The first data generating means includes means for generating first profile data using a position near the apex portion of the heart as a starting point, and the outline setting means includes means for detecting an outline point of each of the first profile data in the first direction away from the apex portion of the heart toward the aortic valve. The outline setting means includes means for re-detecting outline points from a designated position on the long axis as a starting point to a position near the apex portion of the heart along the second position away from the aortic valve toward the apex portion of the heart after outline point detection is performed along the first direction. The threshold value determining means includes means for setting first and second threshold values for left and right sides of the first profile data with respect to the long axis, and the outline setting means includes means for detecting the outline points on the basis of the first and second threshold values on the left and right sides of the long axis. The first profile generating means includes means for determining a minimum value of the first profile data as the inner density, and the position detecting means includes means for detecting a maximum value of the first profile data as the maximum density position.

In the image processing apparatus according to the second aspect of the present invention, when a left ventricle contrast medium image of an object to be diagnosed is given as halftone image data, a long axis connecting, for example, the middle point of the aortic valve and the apex portion of the heart is set, and first profile data representing the pixel values (densities) of pixels constituting the long axis is formed. Second profile data representing a profile on a perpendicular axis perpendicular to the long axis at each pixel position thereon is formed. The background density of the left ventricle of the heart on each of the perpendicular axes is obtained from the second profile data.

More specifically, if an outline point on an adjacent perpendicular axis one line ahead of the current perpendicular axis has already been determined, a position spaced apart from the outline point by a predetermined distance is designated. The background density of the designated outside position is read from the second profile data. If, however, image data includes the data of a structural object such as the rib, the densities of a peripheral portion of the left ventricle of the heart may be low. In such a case, the second profile data does not exhibit a gradual change between the designated outside position and the long axis and has a peak value larger than that of the background density of the designated outside position (provided that the densities of the left ventricle contrast medium image are lower than those of a peripheral portion). For this reason, such a peak value is detected as the maximum variation position. If this peak value is detected, the pixel value of the position corresponding to the peak value is replaced with a background density.

In contrast to this, the representative inner density of the left ventricle of the heart on each perpendicular axis (e.g., the minimum value of the second profile data) is obtained. The weighted mean of the background and inner densities is calculated to calculate outline extraction threshold values for the left and right sides of each perpendicular axis with respect to the long axis. The threshold values and the second profile data are compared with each other within the range from a starting point of outline search located at a predetermined distance outside an outline point of the immediately preceding perpendicular axis to the long axis. As a result, a position corresponding to a pixel value equal to or smaller than a corresponding threshold value is detected as a left ventricle outline point on each perpendicular axis.

With this operation, even if a structural object such as the rib appears near a left ventricle contrast medium image, and the pixel values of the structural object decrease as compared with a normal peripheral portion, background densities which can almost eliminate the influence of the structural object can be automatically determined regardless of the decrease in density, and accurate threshold values can be set. Consequently, the precision of outline extraction improves. Even if the influence of variations in pixel value due to a structural object is large, and the relationship in magnitude between a set threshold value and a background density value is reversed, the starting point of outline search is changed to a position closer to the long axis to avoid a detection error.

According to the second aspect of the present invention, therefore, even if a structural object such as the rib appears near an object to be diagnosed, e.g., the left ventricle of the heart, and the background densities are decreased because of the structural object, an outer density, i.e., a background density, can be accurately selected without being influenced by the decrease in density. Hence, a threshold value can be determined with high precision as in the case wherein no structural object appears in the image. Therefore, an outline can be extracted more accurately and stably with high operation efficiency.

The third aspect of an image processing apparatus according the present invention is, in the first and second aspects, characterized in that the outline extracting means further includes means for performing a subtraction between a first image read from the image memory means and a second image one frame ahead of the first image, means for performing absolute value processing with respect to an image obtained by the subtraction, and means for multiplying the image, which has undergone the absolute value processing, by a predetermined coefficient, and subtracting the resultant image from the first image.

The third aspect of an image processing method according the present inventions, in the first and second aspects, characterized in that the third step further includes the substeps of performing a subtraction between a first image read in the second step and a second image one frame ahead of the first image, performing absolute value processing with respect to an image obtained by the subtraction, and multiplying the image, which has undergone the absolute value processing, by a predetermined coefficient, and subtracting the resultant image from the first image.

Further, in the first to third aspect of the present invention, the image acquiring means includes means for acquiring a contrast image of a radiation image obtained by filling the desired portion with a contrast medium. The image acquiring means includes means for acquiring an X-ray left ventricle contrast medium image at the end of diastole.

With the above arrangement, preprocessing is performed to emphasize even a portion in which the concentration of a contrast medium is low by detecting a change in contrast medium concentration from the previous frame, and a threshold value is obtained with respect to a signal based on the concentration of the contrast medium in the emphasized portion of the left ventricle of the heart, thereby determining an outline point. Therefore, a desired outline can be automatically extracted from even a portion, of the left ventricle of the heart, in which the concentration of the contrast medium is low.

In addition, since the outline of a desired area can be automatically extracted with few operations, correction is not required or need not be performed frequently, and the burden on the operator is reduced.

Furthermore, since the concentration and amount of a contrast medium injected can be minimized, the influence of the side effect of the contrast medium is reduced, and the burden of a person to be examined is reduced.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 2 is a flow chart showing the operation of an outline extractor according to the first embodiment of the present invention;

FIGS. 3A to 3C are views for explaining a method of setting a long axis in the first embodiment;

FIG. 7 is a flow chart showing the operation of an outline extractor according to the second embodiment of the present invention;

FIGS. 18A and 18B are views for explaining inconveniences in the prior art, in which FIG. 18A is a view showing an image of the left ventricle of the heart in which the rib appears, and FIG. 18B is a graph showing a long axis perpendicular profile representing changes in density along a line B–B' in FIG. 18A;

FIG. 19 is a flow chart showing the procedure for a search for the apex portion of the heart according to the second embodiment;

FIG. 23 is a flow chart showing the operation of smoothing of an outline;

FIGS. 24A and 24B are views for explaining a method of smoothing an outline;

FIG. 30 is a block diagram showing the third modification of the profile synthesizing section $3c_1$.

DETAILED DESCRIPTION OF THE PREFERRED EMBODIMENTS

Embodiments of the present invention will be described below with reference to the accompanying drawings.

An image applied to the present invention is not limited to an X-ray contrast medium image, but any image can be applied as long as it consists of pixels having different pixel values on the inside and outside of an object to be diagnosed. For example, images obtained by a nuclear medical diagnosing apparatus, an MRI (magnetic resonance imaging) apparatus, and an X-ray CT apparatus may be applied. Furthermore, the present invention can be applied to a DF (digital fluorography apparatus). For the sake of descriptive convenience, the present invention will be described below with reference to an X-ray diagnosing apparatus as an example.

Assume that in the following embodiments, a diagnosis portion to be diagnosed by X-ray diagnosis is the heart of an object to be examined, and a left ventricle contrast medium image is produced while a contrast medium is injected into the heart.

Figure 1:
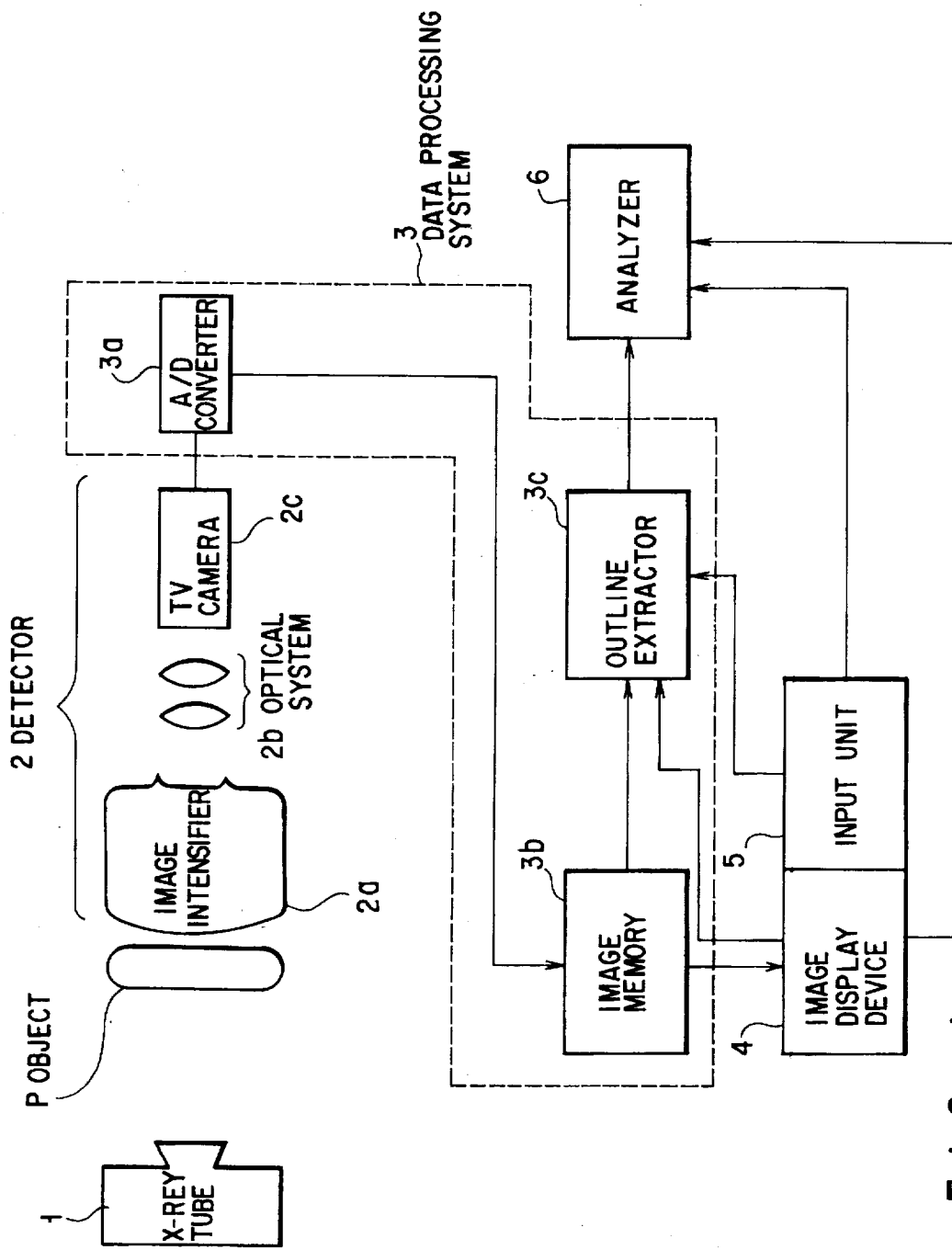
FIG. 1 is a block diagram showing the schematic arrangement of an X-ray diagnosing apparatus including an image processing apparatus according to the first embodiment of the present invention.

FIG. 1 is a block diagram showing the schematic arrangement of an X-ray diagnosing apparatus including an image processing apparatus according to the first embodiment of the present invention.

The X-ray diagnosing apparatus of the present invention includes an X-ray tube 1, a detector 2, a data processing system 3, an image display device 4, an input unit 5, and an analyzer 6.

The X-ray tube 1 radiates X-rays onto an object P. A high-voltage generator (not shown) for applying a high voltage is connected to the X-ray tube 1. The operation of the high-voltage generator is controlled by an X-ray controller (not shown). With this arrangement, the X-ray tube 1 radiates pulse-like X-rays onto the object P.

The detector 2 detect X-rays transmitted through the object P and converts the transmitted X-rays into an image signal.

The detector 2 includes an image intensifier 2a, an optical system 2b, and a TV camera 2c. The image intensifier 2a converts the X-rays transmitted through the object P into visible light. The optical system 2b guides this visible light to the TV camera 2c. The TV camera 2c uses, for example, a CCD element as an image pickup element, and converts the visible light corresponding to the transmitted X-rays into an image signal.

The data processing system 3 for processing the image signal is connected to the TV camera 2c.

The data processing system 3 has an A/D converter 3a, an image memory 3b, and an outline extractor 3c.

The A/D converter 3a converts the image signal, as an analog amount, output from the TV camera 2c into image data as a digital amount. The image memory 3b temporarily stores the image data as the digital amount in units of frames.

The outline extractor 3c receives the image data stored in the image memory 3b, and extracts the outline of a desired portion. The outline extractor 3c incorporates a computer and can execute processing for outline extraction (to be described later).

The image display device 4 includes a display unit such as a CRT. The image display device 4 receives the data stored in the image memory 3b at a predetermined timing in units of frames, and displays an X-ray image of a diagnosis portion of the object almost in real time.

The input unit 5 incorporates, for example, a keyboard, a mouse, a track ball, and the like. The input unit 5 outputs information, e.g., a coordinate input, set by an operator to the outline extractor 3c and the image display device 4, and also outputs a command required for function analysis to the analyzer 6. The input unit 5 may be incorporated in the image display device 4.

The analyzer 6 receives the extracted data from the outline extractor 3c, and performs function analysis of a portion corresponding to the extracted data, e.g., the left ventricle of the heart. For example, function analysis of the left ventricle includes ejection fraction measurement of obtaining the ejection fraction of the heart on the basis of the volume of the ventricle at the end of diastole and the volume of the ventricle at the end of systole which are calculated from outline data, and a cardiac wall motion analysis of obtaining the moving amount of the cardiac wall on the basis of the outline shapes at the end of diastole and the end of systole. This analysis result is displayed on the image display device 4, as needed.

The operation of the first embodiment having the above arrangement will be described below with reference to FIGS. 2 to 6C.

FIG. 2 is a flow chart showing the operation of the outline extractor according to the first embodiment of the present invention.

The outline extractor inputs image data from the image memory 3b (step S1). Assume that this image data is obtained from a contrast medium image while a contrast medium is injected into the left ventricle. When or after this image data is input, the data is filtered by a smoothing filter (low-pass filter) to reduce coarseness due to X-ray noise. While this image data is input, a left ventricle contrast medium image is displayed on the image display device 4.

The outline extractor sets a long axis LA (step S2). The long axis LA is a line segment connecting the middle point (black circle) of the aortic valve to the apex portion (white circle) of the heart, as shown in FIG. 3C. The long axis is set as follows. First, an area where the left ventricle is present is roughly recognized on the image shown in FIG. 3A. The positions of "x" marks are then designated, as shown in FIG. 3B. The set long axis is used to define an area to be subjected to outline extraction processing. The long axis LA is set by designating two points, i.e., the middle point of the aortic valve and the apex portion of the heart shown in FIG. 3C, or three points, i.e., two end points of the aortic valve and the apex portion of the heart, upon moving the cursor on the screen of the image display device 4 by using a mouse, a track ball, or the like (not shown). For example, the long axis LA is set by connecting the middle point of the aortic valve to the apex portion of the heart via a line. With this long axis, an area where the left ventricle is present can be roughly pointed out, and an object to be subjected to outline extraction processing can be defined.

Figure 4:
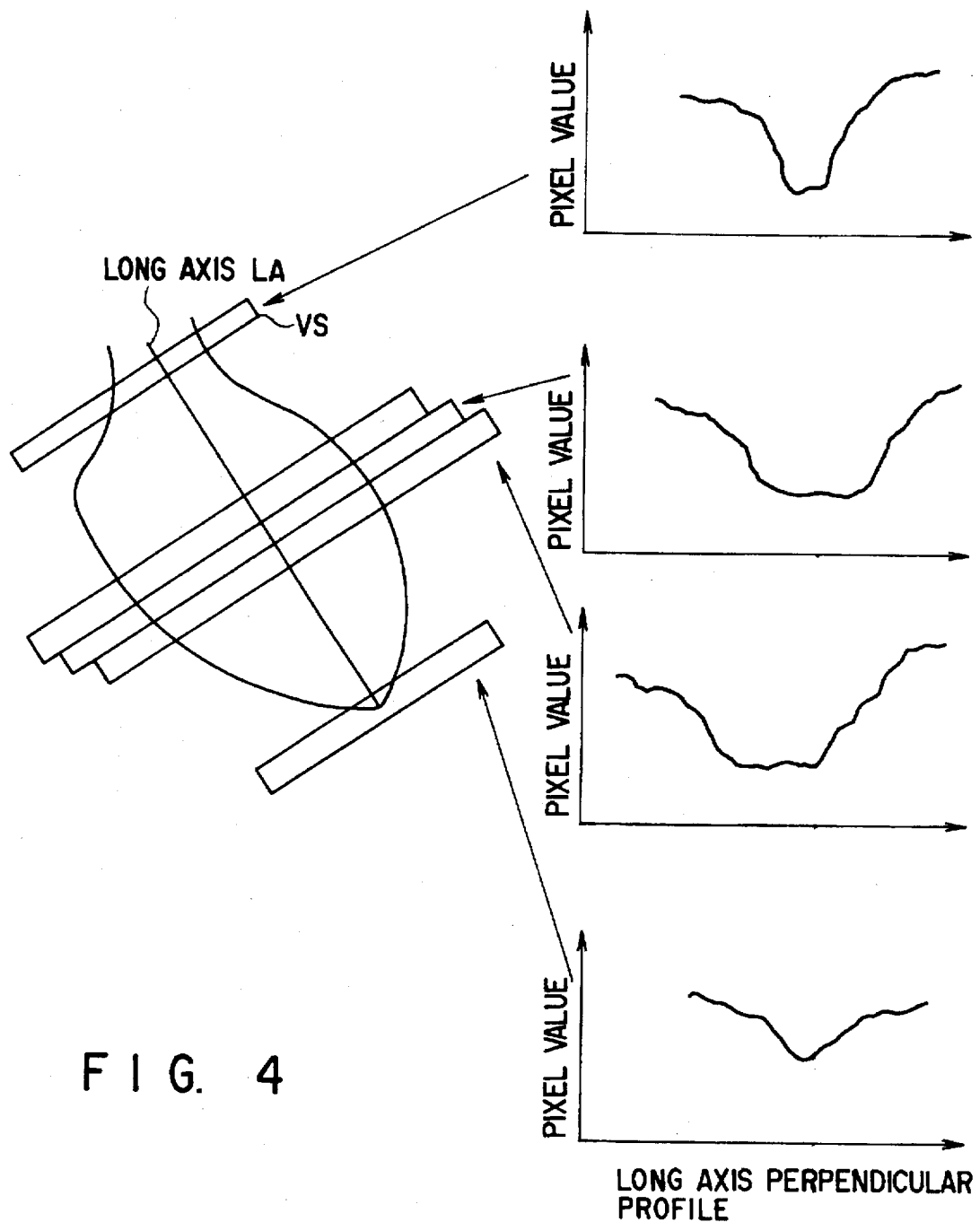
FIG. 4 is a view for explaining a method of dividing an image into areas and generating long axis perpendicular profiles.

A long axis perpendicular profile is generated (step S3). As shown in FIG. 4, long axis perpendicular profiles are generated by drawing a large number of perpendicular lines VS with respect to the long axis LA at almost equal intervals, and obtaining the pixel values on the respective perpendicular lines VS. This means that the target image is divided into partial areas equal in number to the long axis perpendicular profiles.

Figure 5:
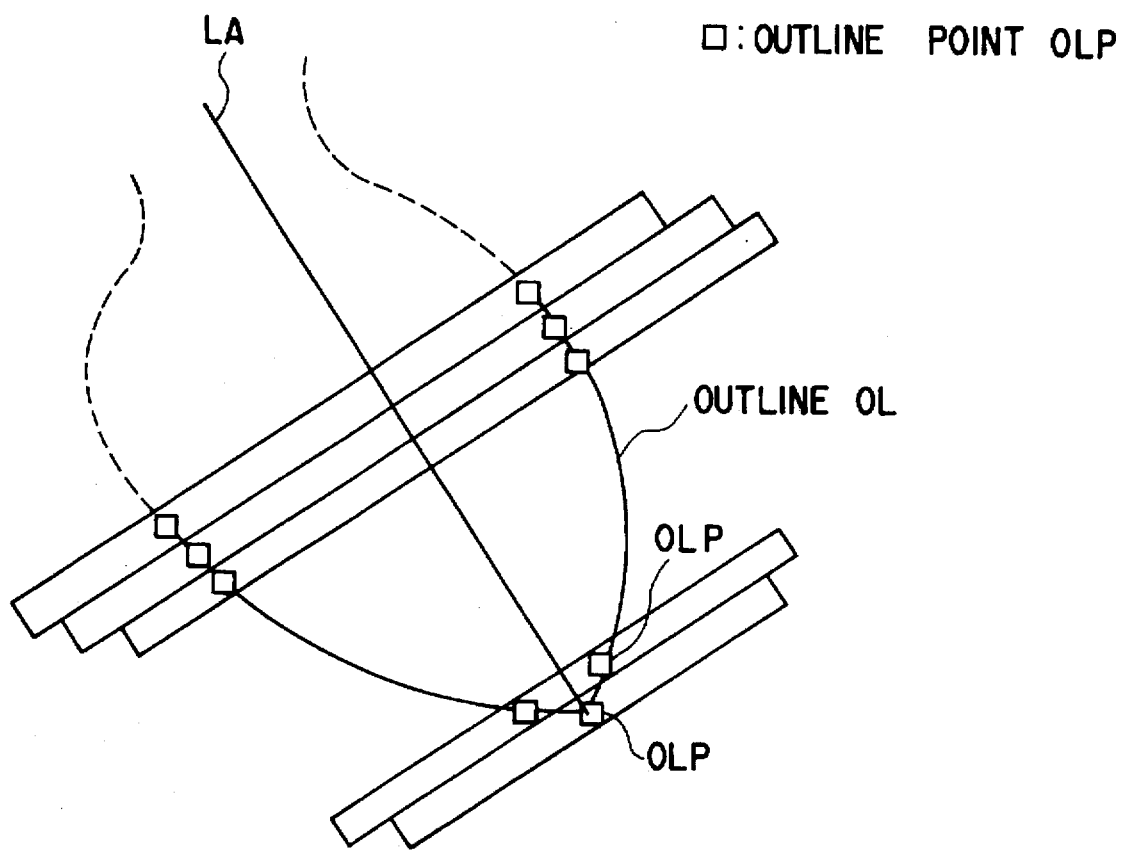
FIG. 5 is a view for explaining a method of extracting an outline in the first embodiment.

As shown in FIG. 5, after the long axis perpendicular profiles are generated, outline points OLP of the left ventricle are sequentially determined, from the apex point of the heart to the middle point of the aortic valve, on the long axis perpendicular profiles, thereby extracting an outline OL. The procedure for this outline extraction will be described below.

Figure 6A:
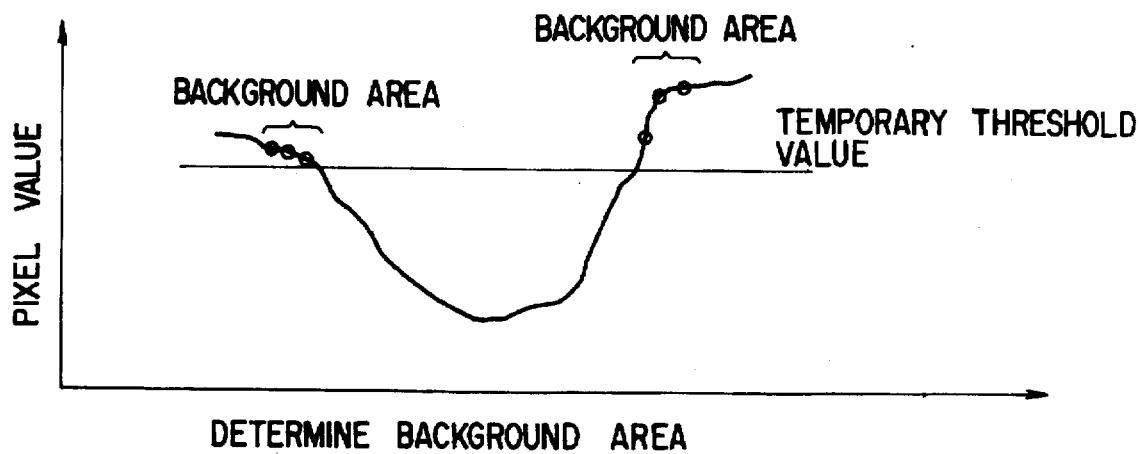
FIG. 6A to 6C are graphs for explaining methods of determining a background area, a threshold value, and an outline point, respectively, in the first embodiment.

A background area is searched (determined) on each long axis perpendicular profile (step S4). In this case, as shown in FIG. 6A, a point having a value larger than a temporary threshold value is obtained in the direction away from the middle point of each long axis perpendicular profile (the intersecting point between the profile and the long axis), and an area at a predetermined distance outside this point is regarded as a background area. As a temporary threshold value, for example, the pixel value of the apex portion of the heart, which is one end point of the long axis, is used.

The densities (pixel values) of the background area are read (step S5). If the background area includes a plurality of pixels, the pixel values of the pixels are averaged, and the mean value is set as the density of the background area.

The inner densities are read (step S6). A point exhibiting the minimum pixel value between the background areas on two sides of each long axis perpendicular profile is defined as an inner area, and the pixel values of the inner area are defined as inner densities.

Figure 6B:
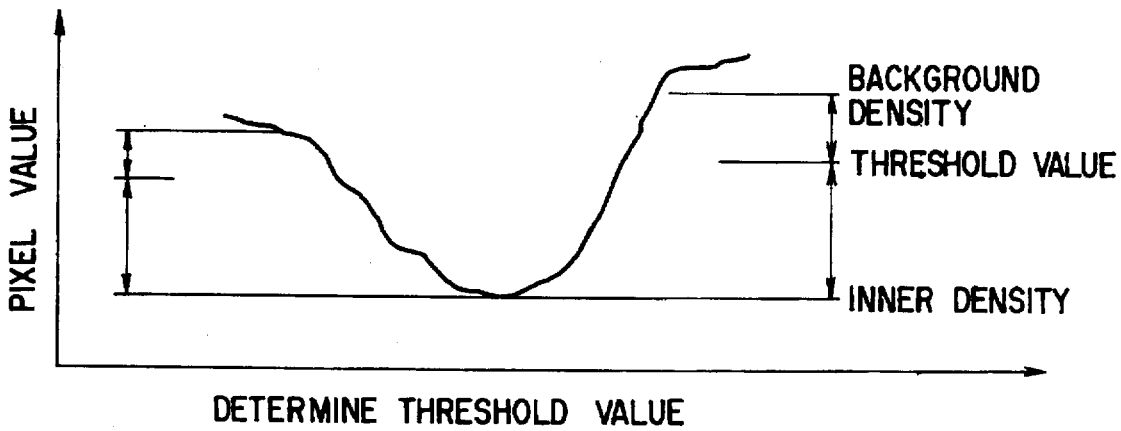

A threshold value for detecting an outline point OLP is determined (step S7). As shown in FIG. 6B, the threshold value is obtained by the weighted mean of the inner densities and the densities of the background area. Weighting coefficients for this weighted mean calculation may be fixed values or variable values which can be arbitrarily changed by the operator.

Figure 6C:
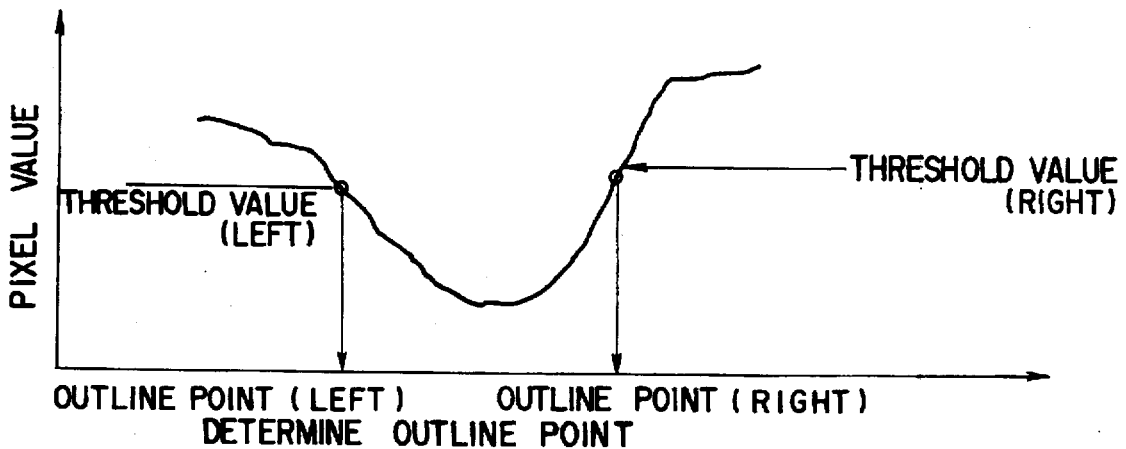

The outline point OLP of the profile is determined by using the threshold value determined in step S7, as shown in FIG. 6C. Pixel values are sequentially checked from the previously determined background area to the middle point of the profile, and the first pixel having a pixel value equal to or smaller than the threshold value is detected as an outline point (step S8). Such outline points are respectively determined on the two sides of the profile.

Steps S4 to S8 are executed with respect to all the long axis perpendicular profiles to detect outline points (step S9). When outline point extraction with respect to all the long axis perpendicular profile is completed, the outline points of the adjacent profiles are connected to each other, and the resultant outline data is output as left ventricle outline (step S10).

According to the first embodiment of the apparatus of the present invention, an X-ray image is divided into partial areas of parallel straight lines; a threshold value suitable for each partial area is determined; and an outline is determined by using this threshold value. Therefore, even if variations or gradients of the densities of a background area (a portion other than a desired area) are larger than those of the densities of a contrast medium image portion as a desired area, a desired outline can be extracted.

According to the first embodiment, the following effects can be obtained in addition to the above effect.

(1) Since the outline of a desired area can be automatically extracted with few operations, the burden of operation can be reduced.

(2) The arrangement of the apparatus can be simplified because there is no need to use an image display mechanism which is used when the operator sets a threshold value while watching threshold values and extracted areas.

(3) Since the time required to adjust a threshold value is not required, the time required for outline extraction is shortened.

(4) Since a contrast medium need not have a high concentration, the amount of contrast medium used is reduced, and the burden on the patient is reduced.

The second embodiment of the present invention will be described below with reference to FIGS. 7 to 10. The apparatus of the second embodiment has the same arrangement as that of the first embodiment, and hence an illustration thereof will be omitted. The same reference numerals in FIG. 7 denote the same parts as in FIG. 2, and a detailed description thereof will be omitted.

FIG. 7 is a flow chart showing the operation of an outline extractor according to the second embodiment of the present invention.

Similar to the first embodiment, in the first embodiment, an image is input, a long axis is set, and long axis perpendicular profiles are generated (steps S1 to S3).

Figure 8:
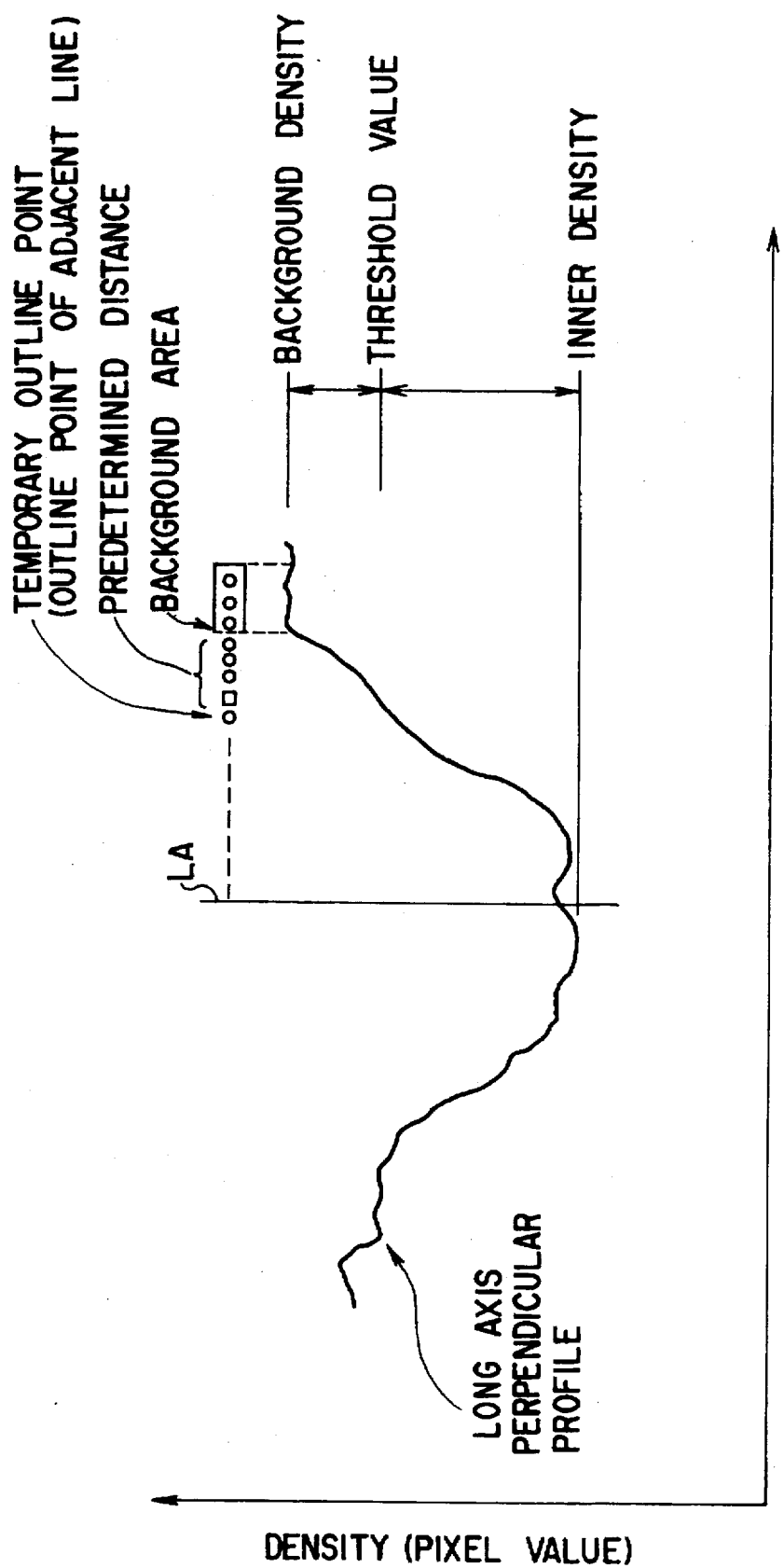
FIG. 8 is a graph for explaining a method of determining a background area in the second embodiment.

The background area of the first profile (i.e., first line) of adjacent profiles whose outline points are not determined is input (step S11). In this case, the operator may set a background area through an input unit 5, or an area having a predetermined positional relationship with the long axis which has been set independently may be automatically set as a background area. More specifically, as shown in FIG. 8, a point of a given profile which is spaced apart from a long axis LA by the same distance as that between a determined outline point of an adjacent profile and the long axis LA is set as a temporary outline point of the profile, and an area at a predetermined distance outside this temporary outline point is determined as a background area. Alternatively, the pixel values of an area at a predetermined distance outside the outline point on the adjacent profile are measured, and the measured values may be set as the background densities of the profile.

Figure 9:
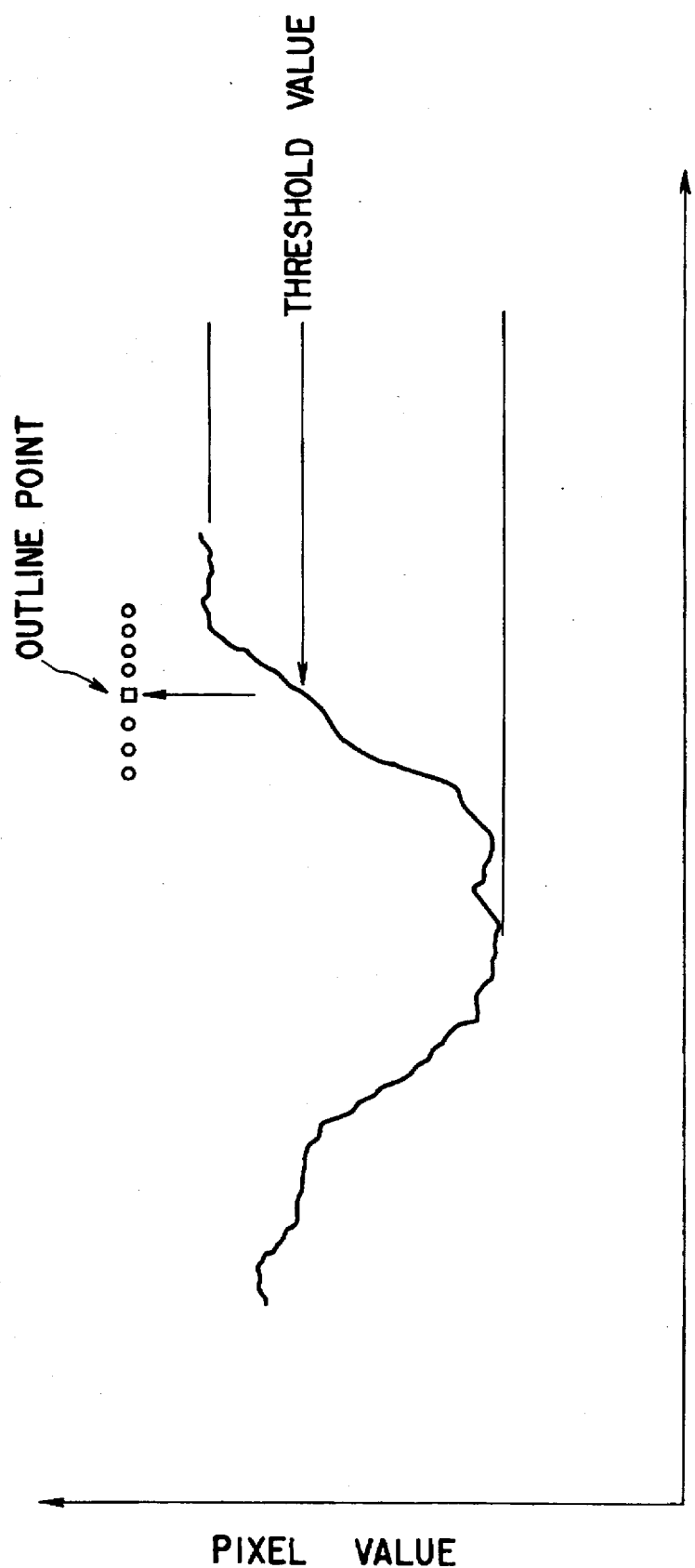
FIG. 9 is a graph for explaining a method of obtaining an outline point in the second embodiment.
Figure 10:
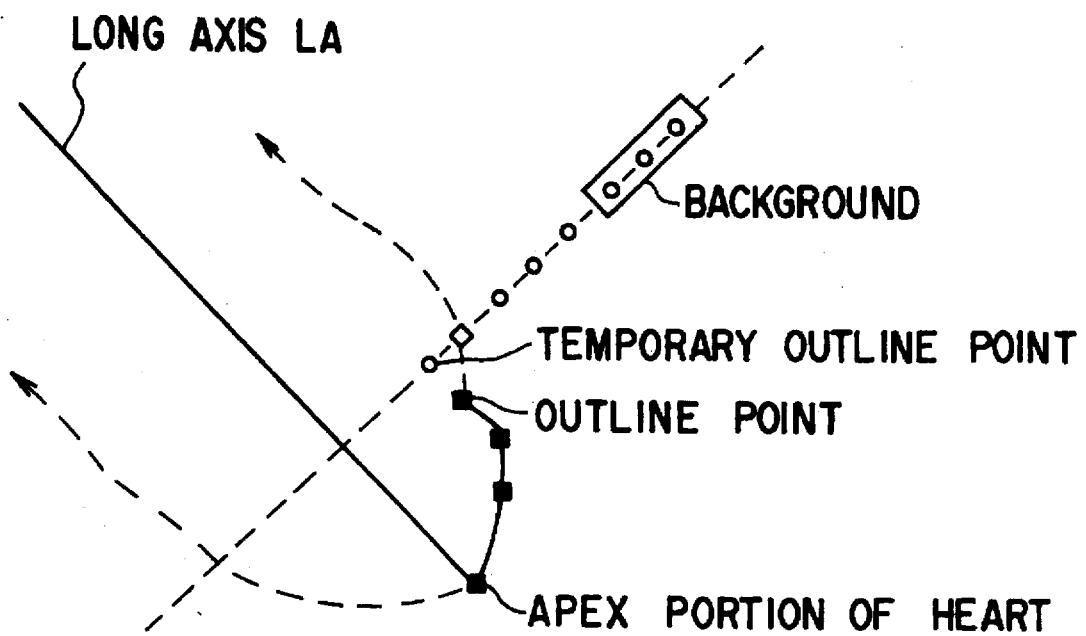
FIG. 10 is a view for explaining a method of extracting the outline of the left ventricle of the heart in the second embodiment.

Similar to the first embodiment, as shown in FIG. 9, an outline point is determined on the basis of a threshold value determined for each profile, and outline points of the left ventricle are sequentially determined, from the apex portion of the heart to the middle point of aortic valve, on the perpendicular profiles. As shown in FIG. 10, the outline points are connected via a line to draw a left ventricle outline (steps S5 to S10).

According to the second embodiment, a desired left ventricle outline can be extracted from even a contrast image in which the left ventricle photographed with the contrast medium overlaps nonuniform background tissue.

Furthermore, in the first and second embodiments, X-rays are used as radiation. However, radiation other than X-rays can also be used. In the above embodiments, an area of interest filled with a contrast medium is extracted from pixels obtained by photography with the contrast medium. However, the above embodiments can be equally applied to contrast images other than a contrast medium image.

The third embodiment of the present invention will be described below with reference to FIGS. 11 to 18B. Since the apparatus of the third embodiment has the same arrangement as that of the first embodiment, an illustration and description thereof will be omitted.

Figure 11:
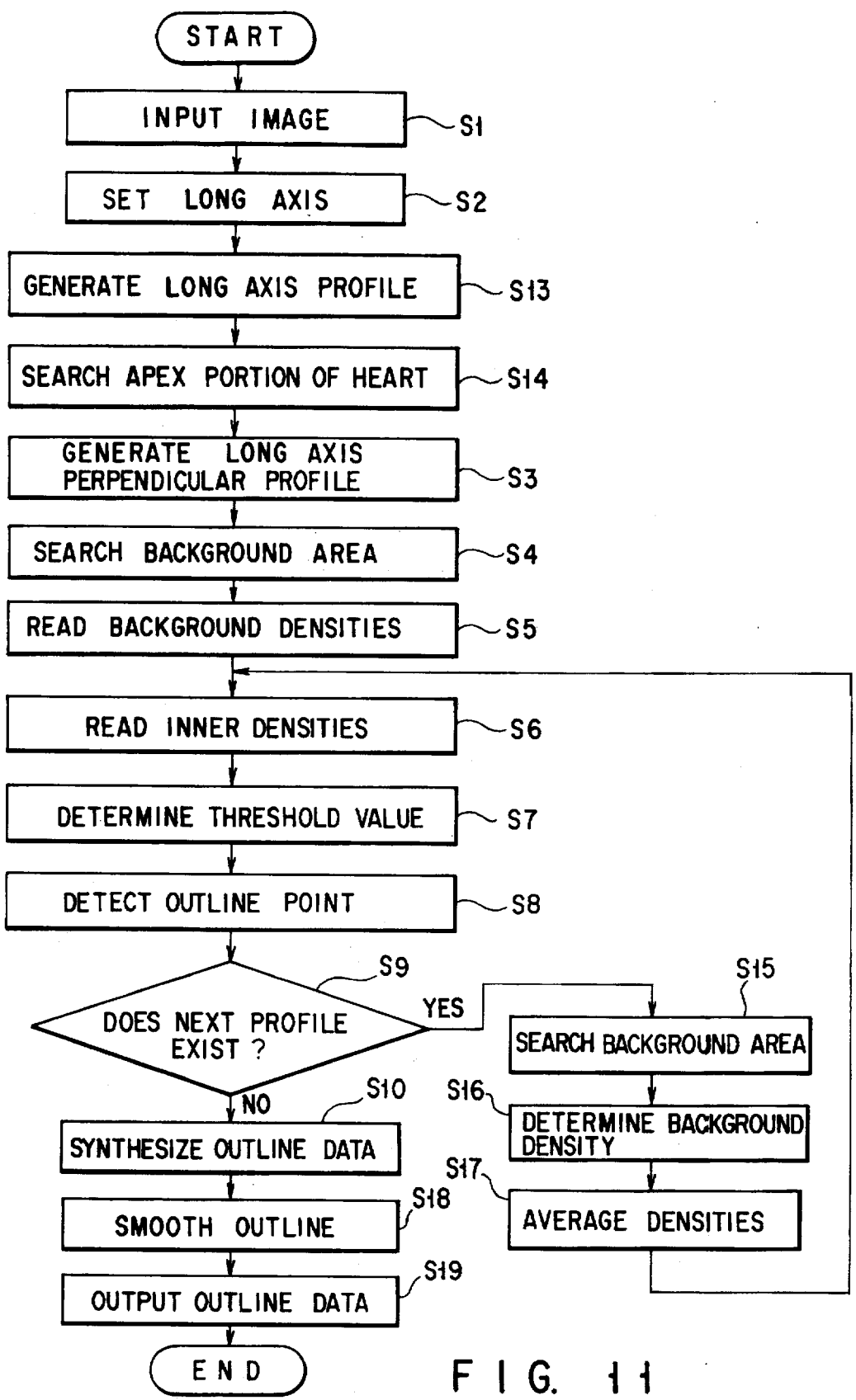
FIG. 11 is a flow chart showing the operation of an outline extractor according to the third embodiment of the present invention.

FIG. 11 is a flow chart showing the operation of an outline extractor according to the third embodiment of the present invention. The same reference numerals in the third embodiment denote the same parts as in the first embodiment, and a detailed description thereof will be omitted.

Image data is input from an image memory 3b (step S1). A long axis LA is set (step S2). In this case, the apex portion of the heart on the long axis LA is a temporary apex portion of the heart.

A density profile (to be referred to as a long axis profile PL hereinafter) with respect to positions (pixels) on the set long axis LA is generated (step S13). The data of the long axis profile PL is generated by reading the densities of the respective pixels on the long axis LA. In obtaining these densities, the long axis LA is extended toward the apex portion of the heart, and density profile data corresponding to this extended portion is also obtained.

The apex portion of the heart is searched (step S14). A point having the maximum primary differential value which is present near a designated point B near the apex portion of the heart is obtained on the basis of the densities of the long axis profile PL. The outline extractor designates a position spaced apart from the point having the maximum primary differential value by a predetermined distance, obtained from the length of the long axis LA, in the direction away from the apex portion of the heart. The outline extractor then reads the density at this designated position together with the minimum value of the long axis profile PL. In addition, the mean value of the read density at the designated position and the minimum density is obtained, and points exhibiting density values smaller than the mean value are sequentially searched from data of the long axis profile PL on the side of the apex portion of the heart. A point AC exhibiting a density value smaller than the mean value is obtained in this manner as the finally determined position of the apex portion of the heart.

A profile (to be referred to as a long axis perpendicular profile PP hereinafter) constituted by a line PE perpendicular to the long axis LA is generated (step S3).

Figure 12:
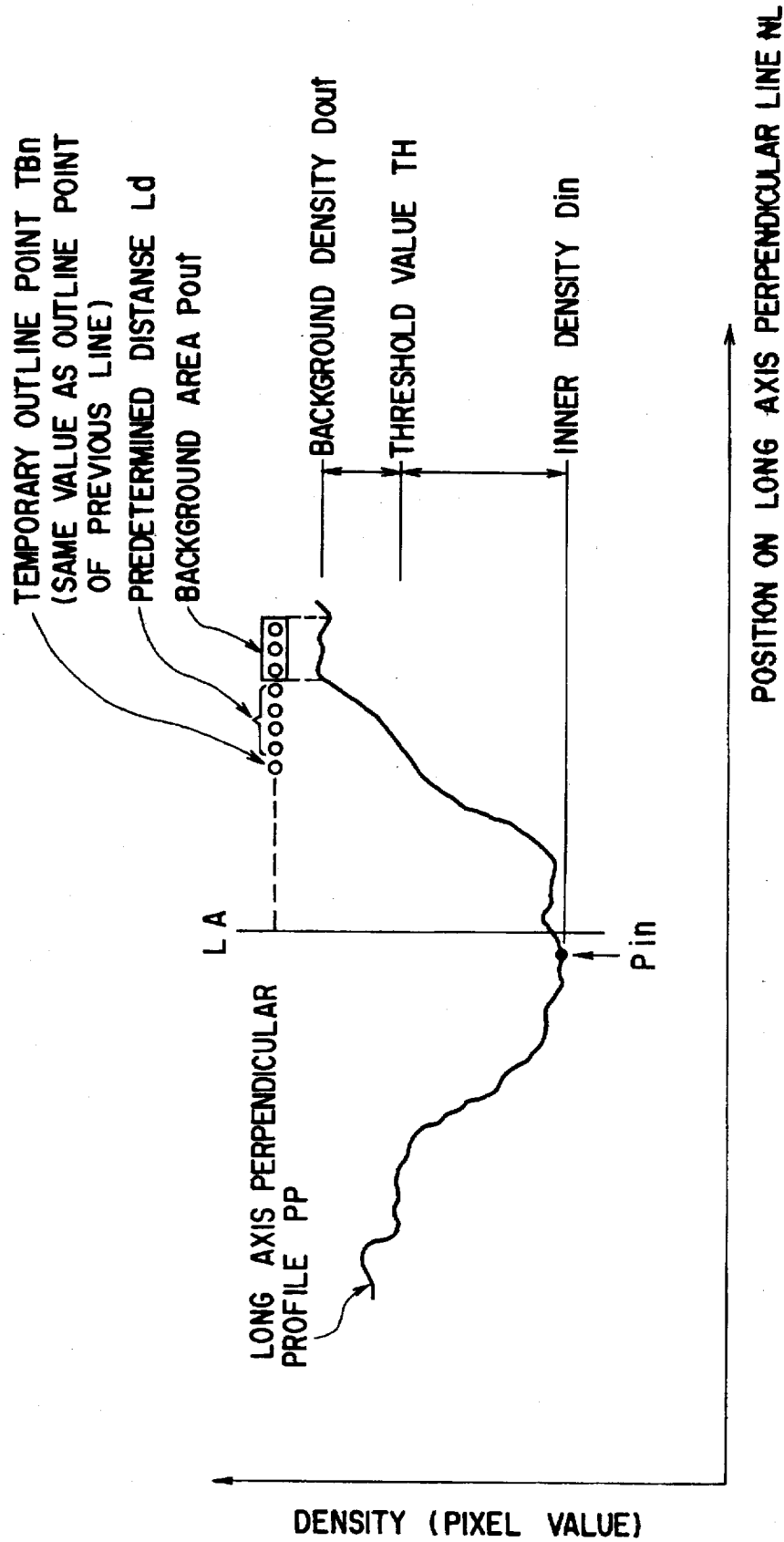
FIG. 12 is a graph for explaining the relationship between a long axis perpendicular profile and a threshold value.

An outline extractor 3c sets the initial position of a background area $P_{out}$ of the long axis perpendicular profile PP, which is provided by the operator through an input unit 5 and becomes the first area to be searched for an outline point (step S4). FIG. 12 shows this state, in which the background area $P_{out}$ is subjected to an outline point search for the second or subsequent line, and the outline point of the previous adjacent long axis perpendicular profile PP is determined. As this initial position, a position at a predetermined distance outside (away from the long axis LA on a perpendicular line NL) the long axis LA may be automatically designated.

The outline extractor 3c reads the densities (i.e., background densities) of the initial background area $P_{out}$ set in step S4 (step S5).

The outline extractor 3c obtains the densities (i.e., inner densities) of an inner point $P_{in}$ (step S6). As shown in FIG. 12, the minimum value on the long axis perpendicular profile PP is obtained as an inner density $D_{in}$. In obtaining this inner density $D_{in}$, a point, on the long axis perpendicular line NL, which is located inside the background area $P_{out}$ (toward the long axis LA) is set as a point to be searched to prevent the influence of a peripheral image portion irrelevant to a left ventricle VS.

The outline extractor 3c determines threshold values for detecting outline points OLP (step S7).

Figure 13:
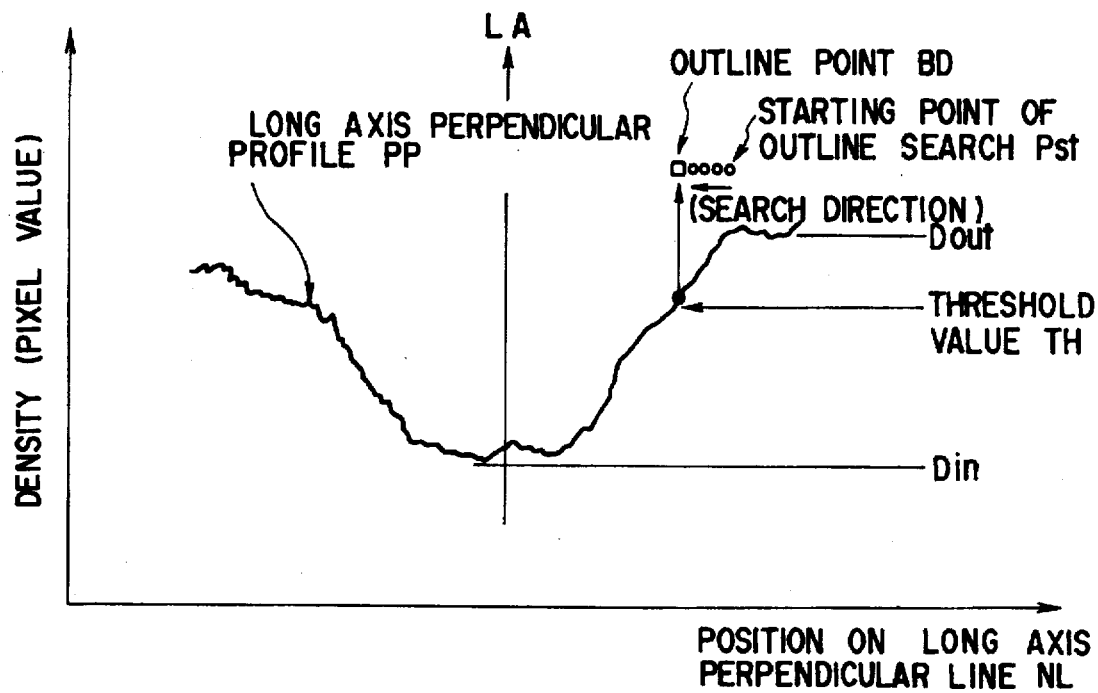
FIG. 13 is a graph for explaining the relationship between a long axis perpendicular profile, a threshold value, a search direction, and an outline point.

The outline extractor 3c independently determines left and right outline points BD on the long axis perpendicular line NL by using threshold values TH for the left and right outline points on the long axis perpendicular line NL which are set in step S7 (step S8). As shown in FIG. 13, a representative position of the set background area $P_{out}$ is set as a starting point $P_{st}$ of outline search, and pixel values are sequentially searched from this starting point $P_{st}$ to the middle point of the long axis perpendicular profile PP. The searched pixel values are then compared with the threshold value TH. The pixel position of a pixel value which becomes equal to or smaller than the threshold value TH first is determined as the outline point BD. Searches for the outline points BD on the long axis perpendicular profile PP are respectively executed on the left and right sides of the long axis LA.

One of the positions in the background area P may be selected as a representative position. In particular, it is desirable to set a pixel located closest to the long axis in the background area P (a point closest to the long axis) or a point located inside of the background area P with one pixel as a representative point.

The outline extractor 3c checks whether any long axis perpendicular profile PP on which outline points BD are to be searched remains, i.e., any pixel remains on the long axis LA (step S9). If YES (a profile remains), steps S15 to S17 and steps S6 to S8 are sequentially executed.

In obtaining an outline point $BD_n$ of the nth line, a temporary outline point $TB_n$ is set (step S15). This temporary outline point $TB_n$ has the same value as that of an outline point $BD_{n-1}$ which has already been determined on the adjacent long axis perpendicular profile PP. That is, the outline point $BD_{n-1}$ of the previous line and the temporary outline point $TB_n$ are separated from the long axis LA by the same distance (see FIGS. 12 and 14). In addition, a position separated outward (in the direction away from the long axis) from a temporary outline point TB by a predetermined distance $L_d$ is set as a background area $P_{out}$ on the nth long axis perpendicular line. The predetermined distance $L_d$ by which the background area $P_{out}$ is shifted outward is adjusted to be a value proportional to the length of the long axis LA. The predetermined distance $L_d$ is set in this manner to set the background area $P_{out}$ at relatively the same position regardless of photographic conditions such as the magnification of an image and the size of an object. As this predetermined distance $L_d$, for example, a value proportional to the matrix size of an image and the magnification of the image may be used.

Figure 15:
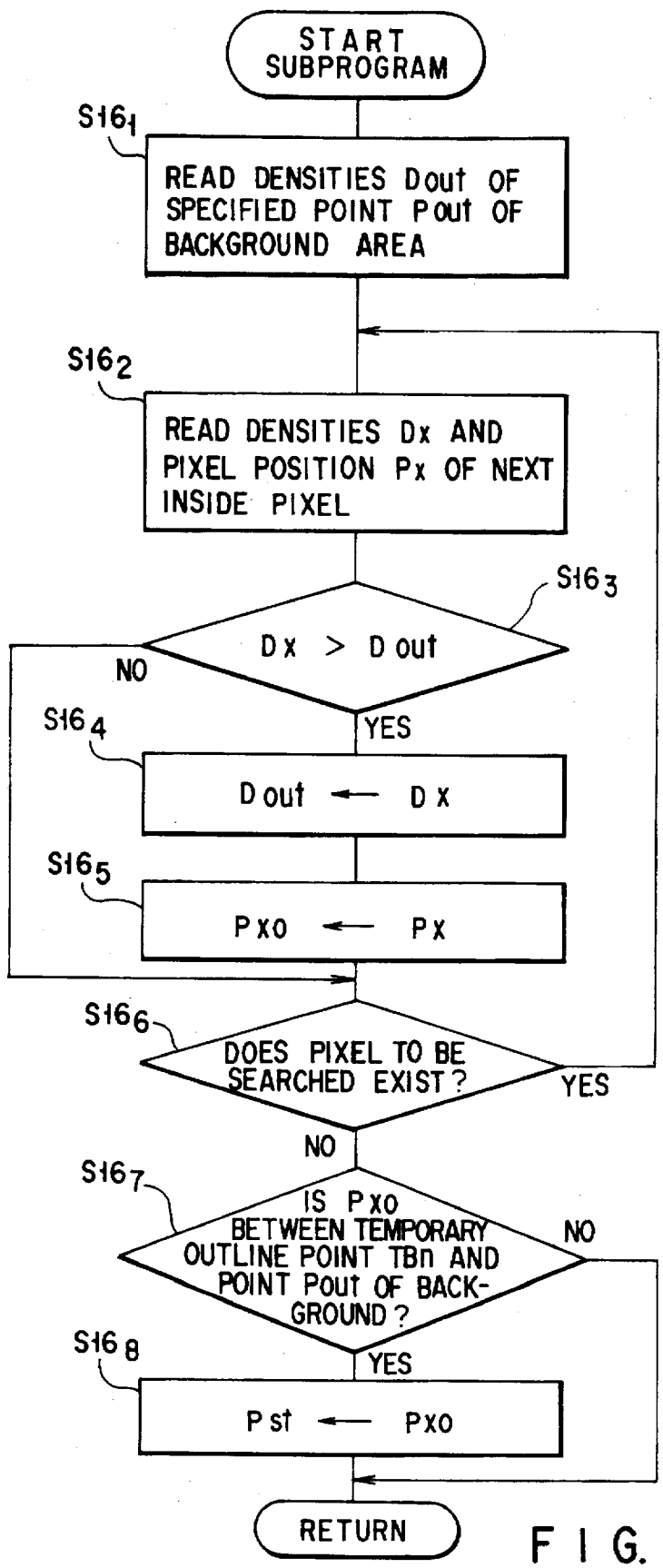
FIG. 15 is a flow chart showing the detailed process of determining a background density in FIG. 11.

Background densities $D_{out}$ are obtained by reading the pixel densities of the designated background area $P_{out}$, and the background densities $D_{out}$ are replaced and the starting point $P_{st}$ is changed, as needed (step S16). The process of reading the background densities $D_{out}$ will be described in detail below with reference to FIGS. 15 and 16A to 16C. FIG. 15 shows a subprogram executed in step S16 in this process.

The outline extractor 3c reads the densities $D_{out}$ of the background area $P_{out}$ designated at the predetermined distance $L_d$ in step S15 (step $S16_1$). Instead of the densities $D_{out}$, the mean value of the densities of a plurality of pixels may be calculated and set.

The outline extractor 3c reads densities $D_x$ and pixel position $P_x$ of a pixel spaced apart inward (toward the long axis) from the background area $P_{out}$ by one pixel (i.e., the pixel at the starting point $P_{st}$ in the first processing) (step $S16_2$). The outline extractor 3c checks whether $D_x > D_{out}$ (where $D_{out}$ are the densities read in step $S16_2$, and $D_x$ are the densities read in step $S16_2$) (step $S16_3$). If NO is obtained in step $S16_3$, i.e., $D_x \leq D_{out}$, pixels on the long axis perpendicular line NL are searched toward the long axis side. In this case, the outline extractor 3c recognizes that there is no pixel having a density value larger than the density values (background densities $D_{out}$) of the background area $P_{out}$, and the flow advances to step $S16_6$ (to be described later).

If YES ($D_x > D_{out}$) in step $S16_3$, the outline extractor 3c recognizes that a structural object such as a rib appears on the image, and there is a pixel having a density higher than the background densities $D_{out}$ of the designated background area $P_{out}$. The flow sequentially advances to steps $S16_4$ and $S16_5$. In step $S16_4$, the background densities $D_{out}$ are replaced with the densities $D_x$ associated with the determination of $D_x > D_{out}$. In step $S16_5$, the position $P_x$ of the pixel exhibiting the density values $D_x$ determined to be larger is replaced with a variable $P_{x0}$.

It is checked whether any pixel to be searched exists on the long axis perpendicular line NL (step $S16_6$). If the pixel search point has not reached the long axis LA (YES), the flow returns to step $S16_2$ to repeat the above processing. If the density value increases as pixels are searched toward the long axis LA, the background density $D_{out}$ is updated by larger values, and the value of the variable $P_{x0}$ representing the pixel position is updated. Therefore, when the search processing to the long axis LA is completed, the background density $D_{out}$ is replaced with a maximum density $D_{max}$, and the pixel position corresponding to the maximum density $D_{max}$ is stored as the variable $P_{x0}$.

If NO in step $S16_6$, i.e., it is determined that the search processing on the long axis perpendicular line NL is completed, it is checked whether the pixel position (the value of the variable $P_{xo}$) corresponding to the maximum density $D_{max}$ is located between the temporary outline point $TB_n$ and the background area $P_{out}$ (step S16$_7$). If NO in step S16$_7$ (e.g., the pixel position corresponding to the maximum density $D_{max}$ is the position shown in FIG. 16B), the flow returns to the main program. If YES in step S16$_7$ (e.g., the pixel position corresponding to the maximum density $D_{max}$ is the position shown in FIG. 16C), the flow returns to the main program after step S16$_8$ is completed. In step S16$_8$, the pixel position (the value of the variable $P_{xo}$) corresponding to the maximum density $D_{max}$ is set as the starting point $P_{st}$ of outline search. As a result, the starting point $P_{st}$ as the position (old) adjacent to the background area $P_{out}$ is automatically replaced with the pixel position (new) corresponding to the maximum density $D_{max}$.

Figure 16A:
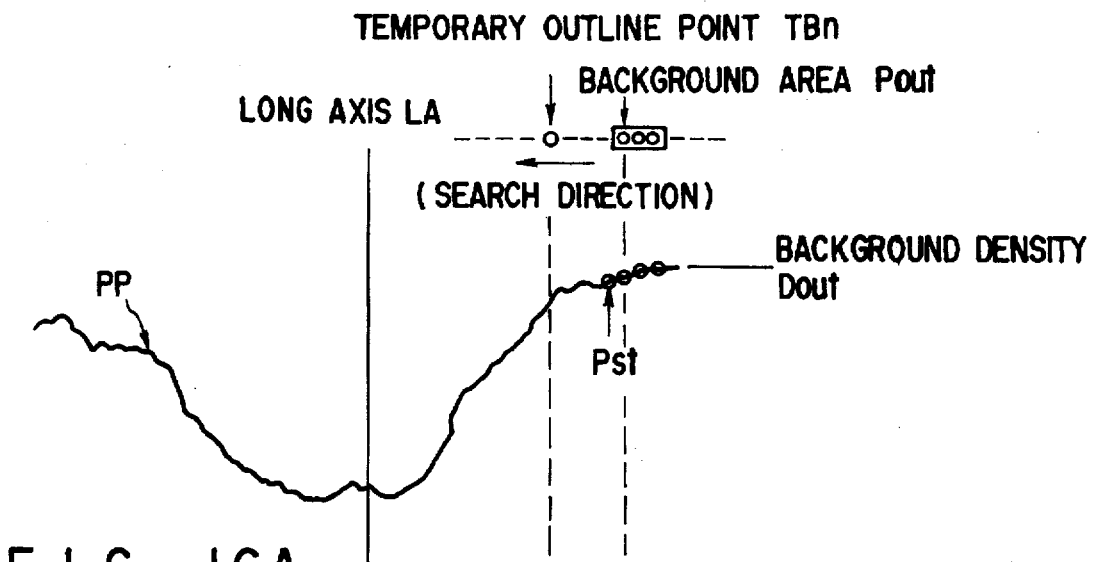
FIGS. 16A to 16C are graphs for explaining the relationship between a long axis perpendicular profile and the maximum density value.

In determining the background density $D_{out}$ in step S16 in the above manner, there are various advantages in considering the maximum density $D_{max}$. If no structural object appears around the left ventricle VS, the density of the long axis perpendicular profile PP generally decreases from the background density $D_{out}$ toward the long axis LA, as shown in FIG. 16A. In this case, even if steps S16$_1$ to S16$_8$ described above are performed, since there is no pixel having a larger density value than the background area $P_{out}$ inside the background area $P_{out}$ (toward the long axis), the density of the background area $P_{out}$ is set as the background density $D_{out}$ (step S16$_1$), and the next pixel of the background area $P_{out}$ is set as the starting point $P_{st}$ of outline search.

Figure 16B:
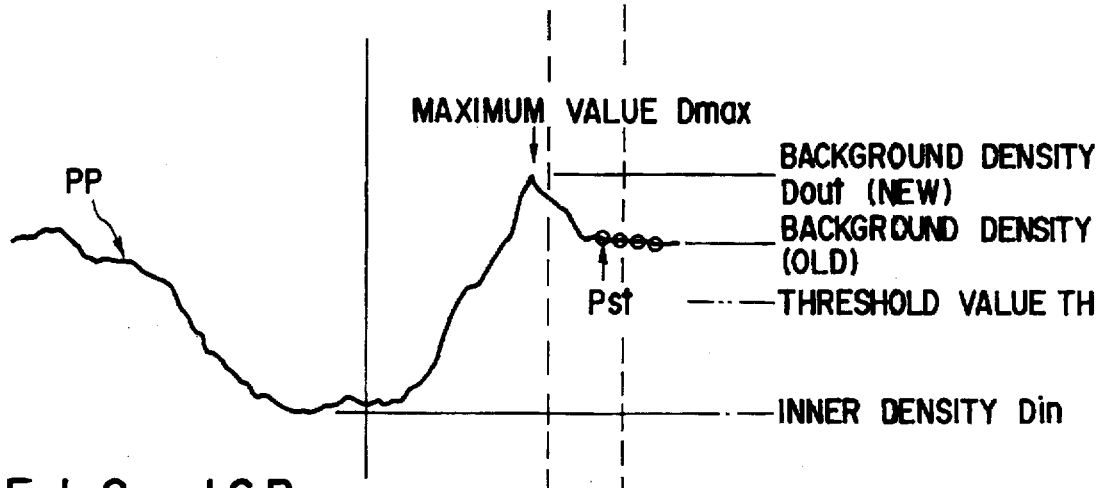
Figure 16C:
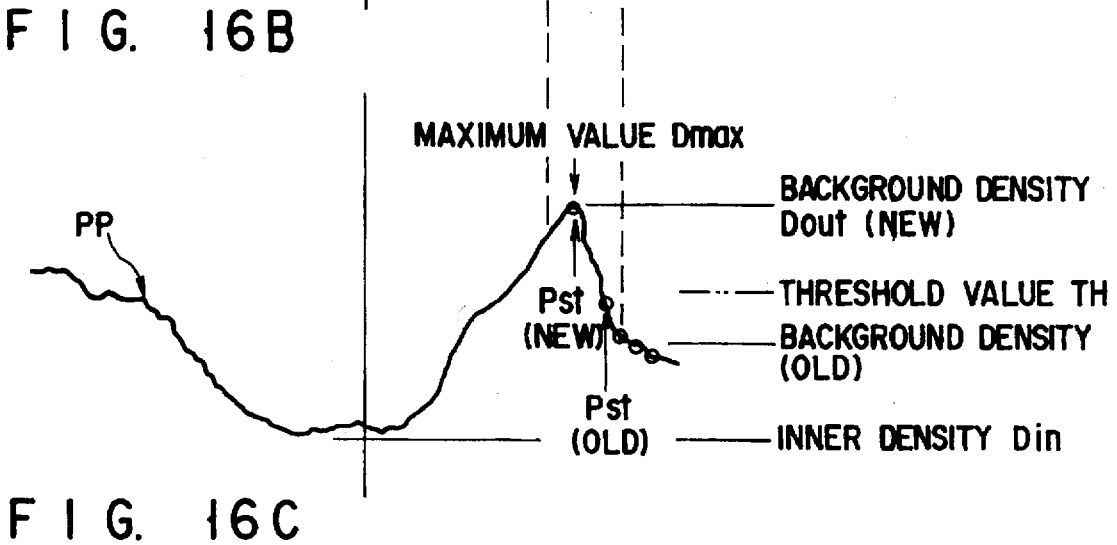

When, however, image data including a structural object or the like is processed, since the densities of pixels representing the structural object are as low as those of the left ventricle VS into which contrast medium is injected, the density of the long axis perpendicular profile PP exhibits its peak between the background area $P_{out}$ and the long axis LA in many cases, as shown in FIGS. 16B and 16C.

When this peak, i.e., the position of the maximum density $D_{max}$ is between the temporary outline point $TB_n$ and the long axis LA as shown in FIG. 16B, for example, the structural object appears at a considerable distance from the left ventricle VS. In general, therefore, the background density $D_{out}$ is still at a relatively high level (a level higher than that of the threshold value TH set in step S7), and a profile curve connecting the maximum density $D_{max}$ and the background density $D_{out}$ is moderate. In this case, the background density $D_{out}$ is simply replaced with the maximum value $D_{max}$. In this manner, the background density $D_{out}$ scarcely affected by the appearance of the structural object is determined.

In contrast to this, when the position of the maximum density $D_{max}$ is between the temporary outline point $TB_n$ and the background area $P_{out}$ as shown in FIG. 16C, the structural object appears very near the left ventricle VS, and the influence of a decrease in pixel value due to the structural object is large. In this case, by performing the processing shown in FIG. 15, the background density $D_{out}$ is replaced with the maximum density $D_{max}$, and the starting point $P_{st}$ of outline search is newly moved to the position of the maximum density $D_{max}$.

When the background density $D_{out}$ is determined in the above manner, the outline extractor 3c shifts the flow of processing to step S14 in FIG. 11. In step S14, the outline extractor 3c calculates the average of the background density $D_{out}$ and the background densities which have already been obtained and determined by using a predetermined number of adjacent long axis perpendicular profiles PP. This mean value is finally set as the current background density $D_{out}$. With this operation, a background density can be stably obtained with high precision. The predetermined number of profiles is proportional to the length of the long axis LA.

Figure 14:
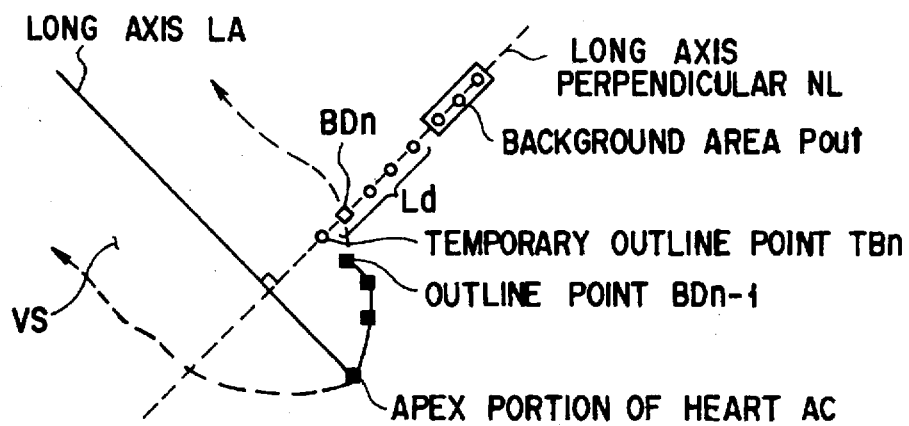
FIG. 14 is a view for explaining a search for an outline point of the left ventricle of the heart.

After the execution of step S17, the flow returns to step S6 again. With this operation, reading of inner densities $D_{in}$ in step S6, determination of threshold values TH in step S7, and detection of outline points BD in step S8 are repeated. Consequently, as shown in FIG. 14, outline points BD are sequentially determined for each long axis perpendicular profile PP (two outline points on the left and right sides of the long axis LA at a time).

If NO in step S9, i.e., if it is determined that detection of outline points on all the long axis perpendicular profiles PP on the long axis LA is completed, the processing in steps S10 to S19 is performed.

Figure 17:
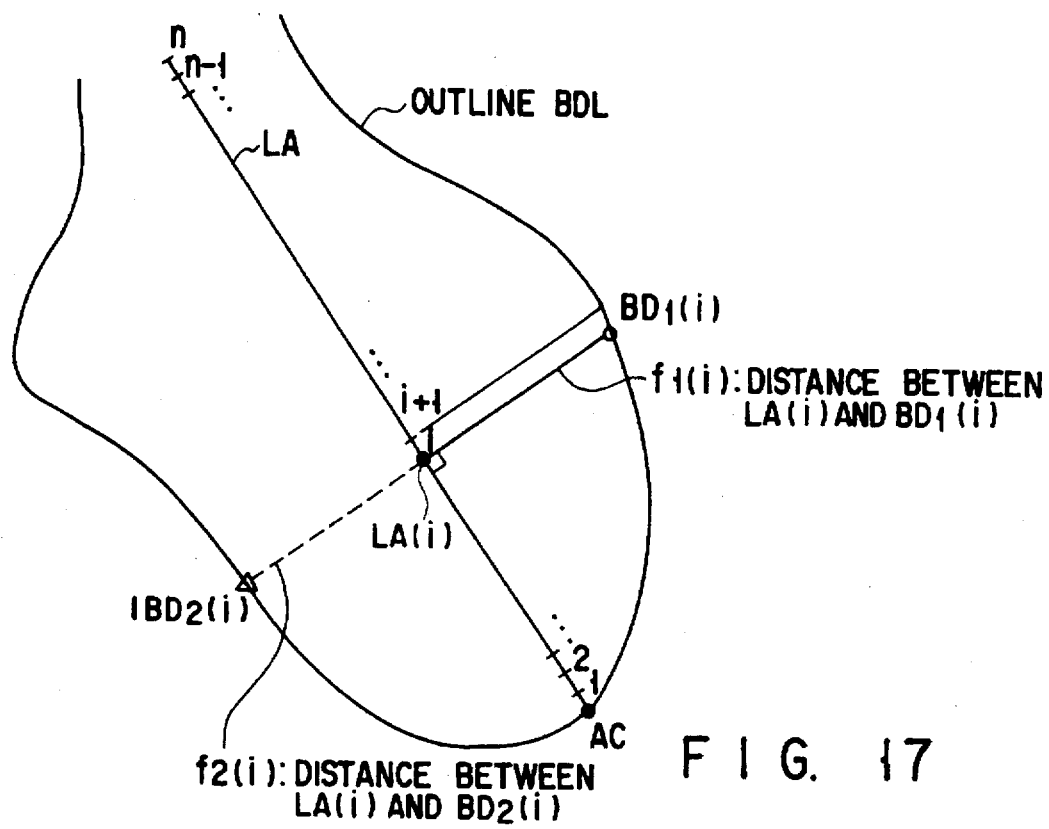
FIG. 17 is a view for explaining an outline point of the left ventricle of the heart with reference to the distance from the long axis.

The outline extractor 3c connects the outline points BD on the respective long axis perpendicular lines to form the data of an outline BDL, as shown in FIG. 17 (step S10). This outline data is held as a value indicating the vertical distance from each point (each pixel) of the long axis LA to a corresponding outline point BD. For example, with regard to the ith pixel LA(i) (a black circle in FIG. 17) on the long axis LA in FIG. 17, the outline data is held as data indicating lengths (distances) $f_1(i)$ and $f_2(i)$ between the position of the ith pixel and the positions (outline points BD1(i) represented by a white circle and BD2(i) represented by a white triangle) where vertical lines extending from the pixel position cross the outline BDL on the two sides of the long axis.

The outline BDL is smoothed by averaging the outline data by using values at the respective points on the long axis LA and predetermined peripheral points (step S18). The range of the predetermined points used for this smoothing operation is set, for example, in proportion to the length of the long axis LA. Since the outline data is held as lengths from the long axis LA, even a two-dimensional graphic pattern, i.e., an outline, can be properly smoothed by one-dimensional arithmetic processing, and a smooth outline can be obtained.

When the smoothing operation is completed, the data of the outline BDL is sent to an image display device 4. For example, this data is superposed/displayed on an X-ray image. The data is also output to an analyzer 6 (step S19). The analyzer 6 performs function analysis of the left ventricle on the basis of the outline data extracted by the outline extractor 3c in the above-described manner.

In the third embodiment, with the above-described image processing, when no structural object appears on an X-ray image, and the long axis perpendicular profile PP has a moderate curve like the one shown in FIG. 16A, the threshold value TH is determined on the basis of the densities of the background area $P_{out}$ and the inner point $P_{in}$. Pixel positions of pixels having densities equal to or lower than the threshold value TH are sequentially detected as the outline points BD (see FIG. 13).

In contrast to this, when a structural object appears on an X-ray image, and the long axis perpendicular profile PP has a peak as shown in FIG. 16B or 16C, the background density $D_{out}$ and the starting point $P_{st}$ of outline search are properly determined without being influenced by the structural object.

In order to explain the advantages of the third embodiment of the present invention, a decrease in the threshold value TH due to the influence of a structural object will be described below with reference to FIGS. 18A and 18B.

Figure 18A:
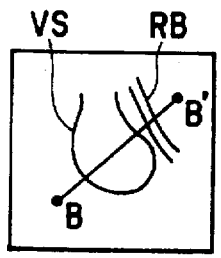
Figure 18B:
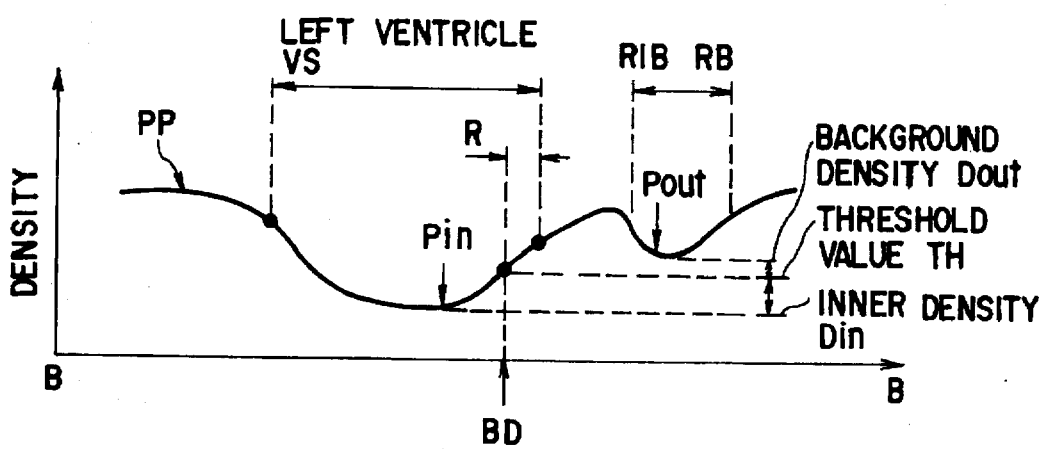

As shown in FIG. 18A, when an image includes not only the left ventricle VS but also a rib RB as a structural object, the long axis perpendicular profile PP along a line B–B' in FIG. 18A has, for example, a curve like the one shown in FIG. 18B. Since the density of a portion corresponding to the rib RB is low, if the background area $P_{out}$ overlaps the portion corresponding to the rib RB, the threshold value TH associated with the weighted mean of the background densities $D_{out}$ (the densities of the background area $P_{out}$) and the inner densities $D_{in}$ becomes smaller than a normal value set when no structure object appears. As a result, the outline point BD determined by the threshold value smaller than the normal value does not represent a true outline point of the left ventricle VS, and a detection error corresponding to a distance R in FIG. 18B occurs.

In the third embodiment of the present invention, such a detection error can be removed in the following manner.

When a structural object appears at a considerable distance from the left ventricle VS, or is small in size, the influence of the structural object on a decrease in pixel value is small. Such a state is discriminated by using the pixel position of the maximum density $D_{out}$ as a parameter. More specifically, as shown in FIG. 16B, when the pixel position of the maximum density $D_{out}$ is far from the background area $P_{out}$, the influence of the structural object on a decrease in pixel value is small. In this case, in order to substitutionally correct the decrease in pixel value, the background density $D_{out}$ is replaced with the maximum density $D_{max}$. This operation serves to reliably prevent a decrease in the threshold value TH determined by the weighted mean of the background densities $D_{out}$ and the inner densities $D_{in}$. Consequently, erroneous detection of outline points described with reference to FIGS. 18A and 18B can be prevented, and an outline can be drawn with high precision.

When a structural object is near the left ventricle VS or large in size, and the pixel position of the maximum density $D_{max}$ is near the background area $P_{out}$ as shown in FIG. 16C, the influence of the structural object on a decrease in pixel value is considerably large. In this case, the background density $D_{out}$ is replaced with the maximum density $D_{max}$ to prevent a decrease in the background density $D_{out}$, and the starting point $P_{st}$ of outline search is moved to the position of the maximum density $D_{max}$. With this operation, a more accurate threshold value TH scarcely influenced by the structural object can be set, and hence the outline point BD can be detected with high precision. Assume that the threshold value TH which is accurately set is larger than the value of the background density $D_{out}$ (old), as shown in FIG. 16C. In this case, a point detected first as a point having a pixel value smaller than the threshold value TH is set as an outline point in step S8. As a result, the starting point $P_{st}$ is erroneously detected as the outline point BD. In this embodiment, however, since the starting point $P_{st}$ of outline search is shifted to the position of the maximum density $D_{max}$, such erroneous detection can be prevented. That is, a pixel position detected first as a position exhibiting a pixel value equal to or smaller than the threshold value TH within a range closer to the long axis than the position of the maximum density $D_{max}$ is accurately determined as the outline point BD.

In addition, according to the third embodiment, since the outline of a desired area can be automatically drawn with a smaller operation amount, the burden of operation on the operator can be greatly reduced. Limitations on positioning in a photographing operation are eased, and the time required for positioning for a photographing operation is shortened. In addition, the efficiency of examination improves.

Furthermore, since limitations on positioning are eased, the patient need not take a difficult posture in a photographing operation. As a result, the burden on the patient is greatly reduced, thus obtaining a secondary effect.

The fourth embodiment of the present invention will be described below with reference to FIGS. 19 and 20A to 20E. The fourth embodiment is related to an improvement in a search for the apex portion of the heart in the third embodiment. The same reference numerals in the fourth embodiment denote the same parts as in the third embodiment, and a description thereof will be omitted or simplified.

An outline extractor 3c performs the processing shown in FIG. 19 in step S14 in FIG. 11 in the third embodiment.

Figure 20A:
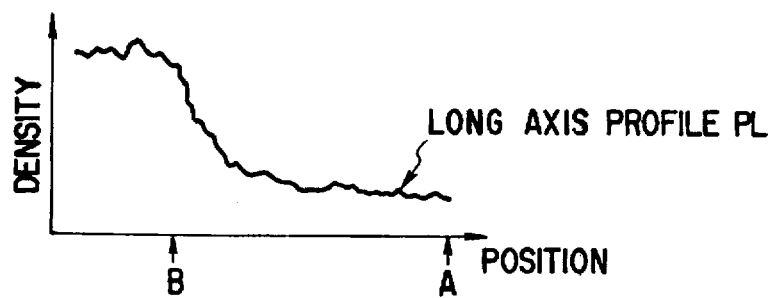
FIGS. 20A to 20E are graphs showing the procedure for the search for the apex portion of the heart in FIG. 19.
Figure 20B:
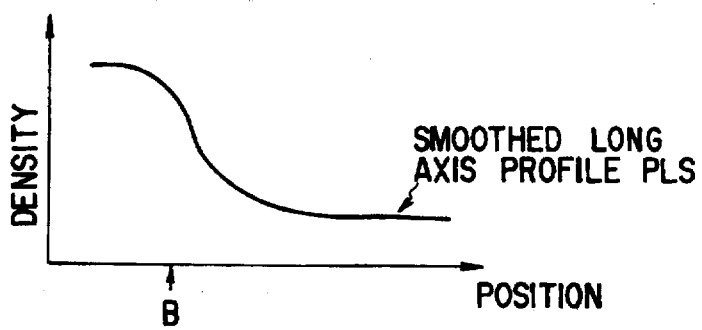

The data of a long axis profile PL (see FIG. 20A) generated in step S13 is smoothed by calculating the mean value of the data and the values of adjacent pixels, as shown in FIG. 20B, thereby generating a smoothed long axis profile PLS (step S14₁).

Figure 20C:
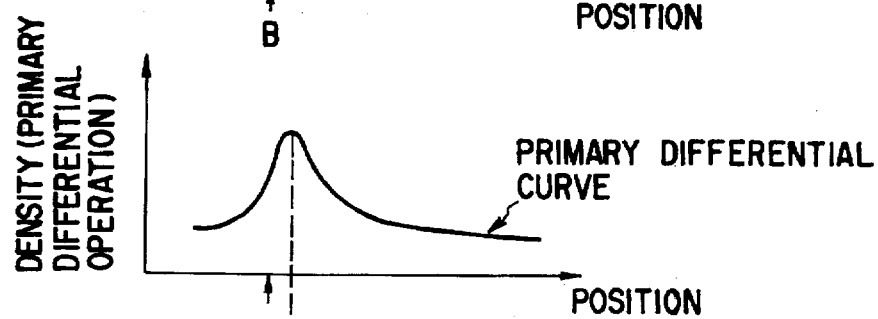
Figure 20D:
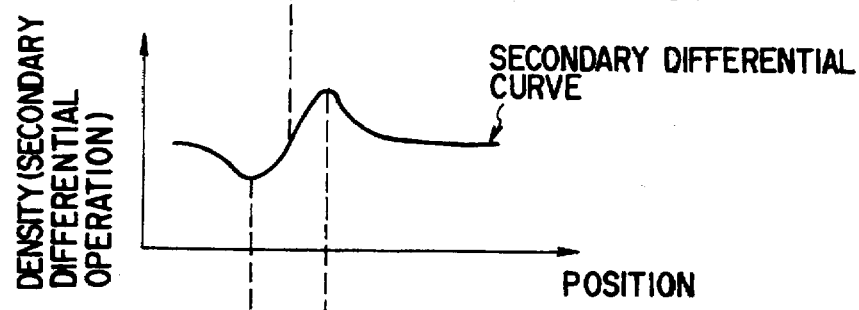

The primary differential operation value of the smoothed data is calculated, as shown in FIG. 20C (step S14₂). With this operation, a peak exhibiting the maximum value appears near a position B of the apex portion of the heart which is set by the operator.

The peak obtained in step S14₂ is specified as the position of the maximum value (step S14₃).

The primary-differentiated profile data is differentiated again (step S14₄). This secondary differential operation exhibits the minimum and maximum points, as shown FIG. 20D.

The outline extractor 3c specifies the minimum and maximum points of the secondary differential operation which are present on both sides of the maximum value of the primary differential operation obtained in step S14₃ (step S14₅).

The outline extractor 3c reads the densities of the maximum and minimum positions of the secondary differential operation, which are specified in step S14₅, on the smoothed long axis profile PLS (step S14₆).

The weighted mean of the two read densities is obtained (step S14₇).

Figure 20E:
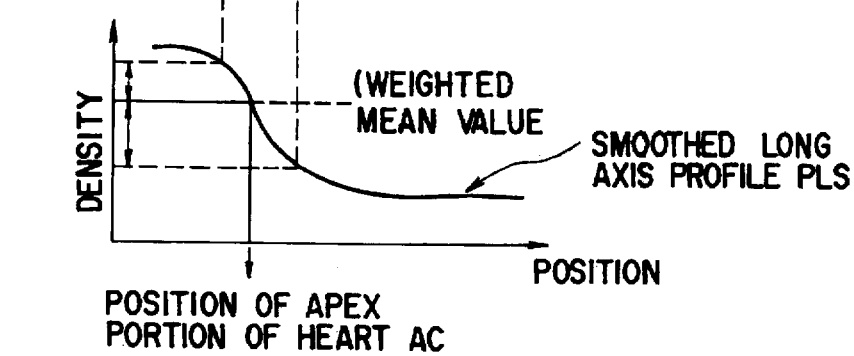

The position corresponding to the weighted mean between the positions corresponding to the minimum and maximum values of the secondary differential operation is automatically set as the position of the apex portion of the heart, as shown in FIG. 20E (step S14₈).

After the position of the apex portion of the heart is automatically set in the above manner, the same processing as that in the third embodiment is performed, and hence an illustration and description thereof will be omitted.

As described above, according to the fourth embodiment, since the position of the apex portion of the heart can be automatically set, the operator only needs to designate a position near the apex portion of the heart in a search for the apex portion of the heart. Therefore, the apex portion of the heart can be designated with high precision as compared with a case wherein the apex portion of the heart is manually designated, and the burden of operation on the operator an be reduced. In addition, the operation efficiency greatly improves.

The fifth embodiment of the present invention will be described with reference to FIGS. 21 and 22A to 22C.

The fifth embodiment is related to a further improvement in an outline search method.

Figure 21:
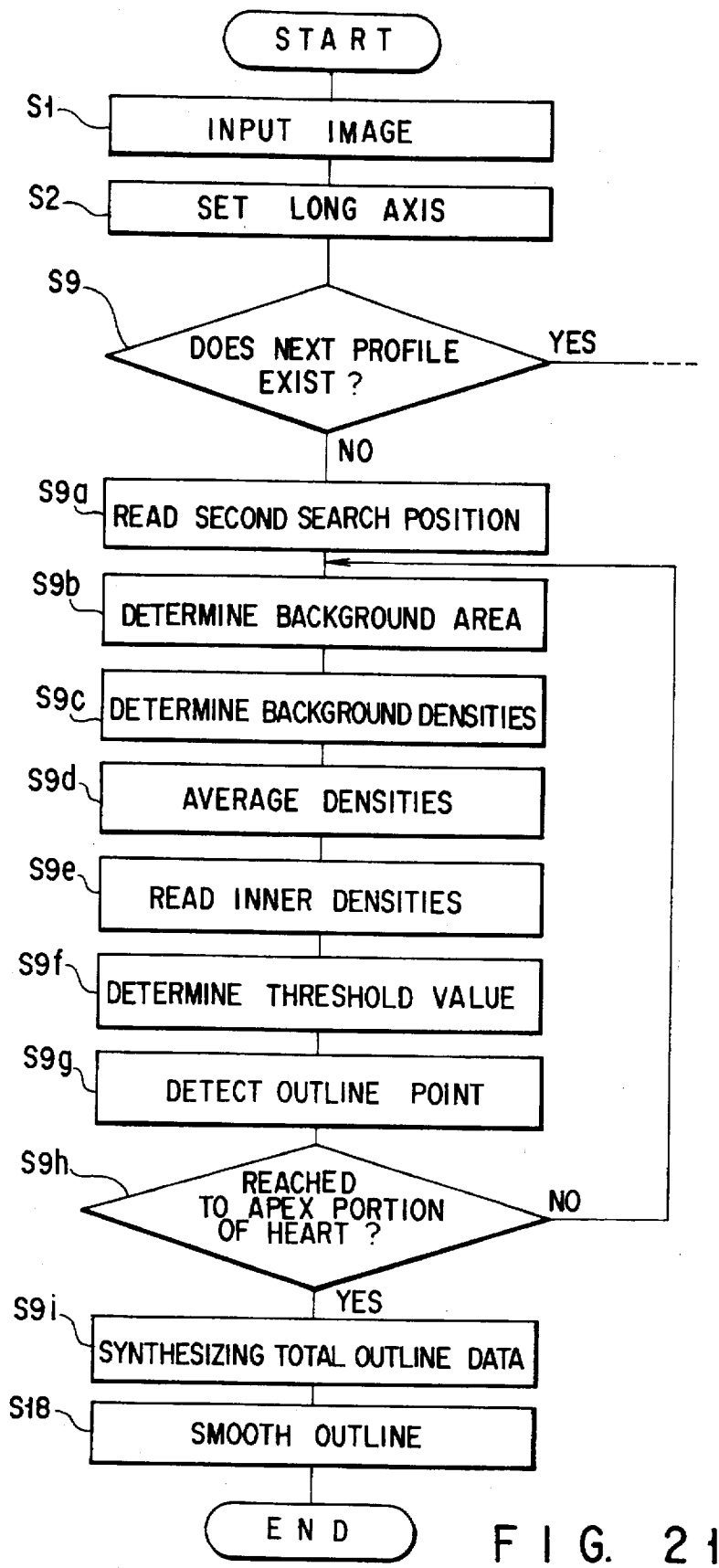
FIG. 21 is a partial flow chart showing the procedure for a re-search for an outline according to the third embodiment.

An outline extractor 3c sequentially performs the processing shown in FIG. 21 after the processing in step S9 in FIG. 11.

Figure 22A:
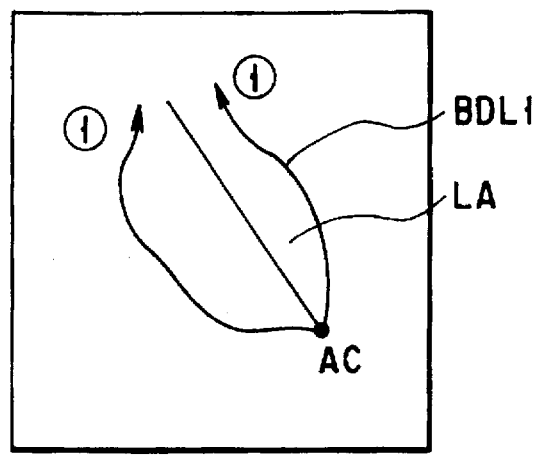
FIGS. 22A to 22C are graphs for explaining the re-search for an outline in FIG. 21.
Figure 22B:
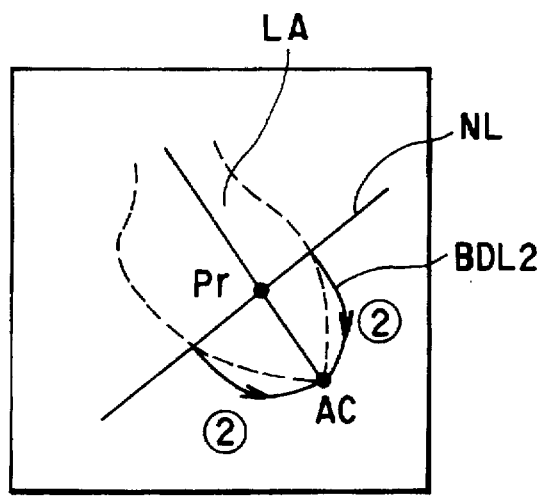
Figure 22C:
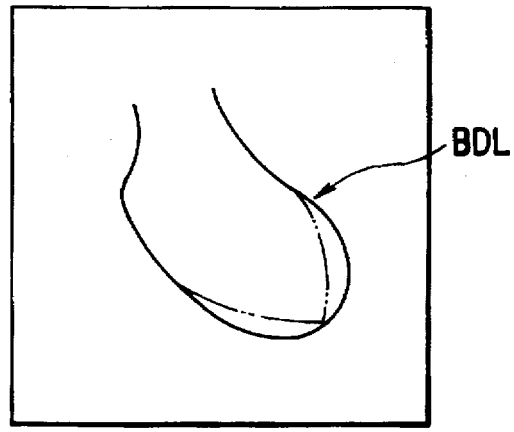
Figure 25:
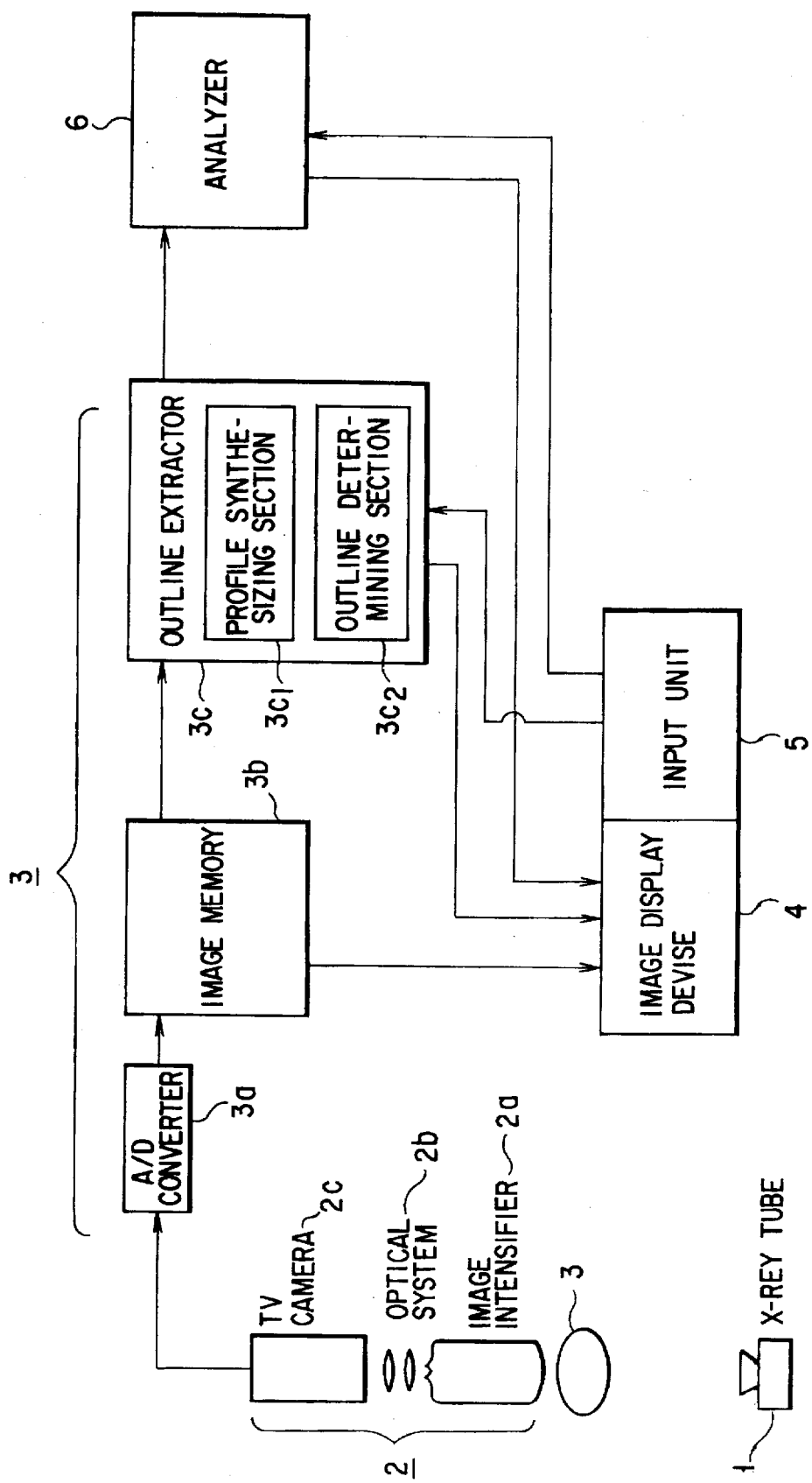
FIG. 25 is a block diagram showing the schematic arrangement of an X-ray diagnosing apparatus including an image processing apparatus according to the sixth embodiment of the present invention.

Assume that in step S9 in FIG. 21, similar to the third embodiment, the outline extractor 3c checks whether any profile PP for which an outline search is to be performed remains on a long axis LA, and determines that the search processing is completed (NO). In this case, as shown in FIGS. 22A to 22C, the first outline search from the apex portion of the heart to the valve is completed, and the associated data of an outline BDL2 is prepared. In the fifth embodiment, After this first search, a second search associated with the processing in step S9a and the subsequent steps is performed from a predetermined position in the reverse direction (i.e., from the position of the valve to the position of the apex portion of the heart).

The outline extractor 3c reads a second search position Pr (step S9a). This search position Pr preferably corresponds to the middle position of a long axis LA, but is not limited to this. For example, the search position Pr may be the end position of the long axis LA which corresponds to the position of the valve.

When this second search position Pr is determined, outline points BD are detected toward the apex portion of the heart in the reverse direction, similar to the third embodiment, as indicated by steps S9b to S9h in FIG. 21 (see the arrows in FIG. 22B).

When it is determined that the search to the apex portion of the heart in the reverse direction is completed (step S9h), the flow advances to step S9i to correct the outline BDL1 detected by the first search by using an outline BDL2 detected by the second search (for example, using the outline BDL2 as a true value), thereby generating the data of an outline BDL, as shown in FIG. 22C.

In the first search, since especially an outline portion near the apex portion of the heart is round, the distance between an outline point of this portion and the long axis increases, an error tends to occur in detection of an outline portion near the apex portion of the heart. In the fifth embodiment, however, an outline portion near the apex portion of the heart can be properly corrected by a second search in the reverse direction. That is, an outline portion (the chain double-dashed line portion in FIG. 22C) detected by the first search in FIG. 22C can be removed from normal outline data. With this operation, the outline of the heart can be drawn with higher precision. In this case, by setting the second search position at a proper position near the apex portion of the heart, only a required portion can be searched to minimize an increase in drawing time.

In the first to fifth embodiments, the left ventricle portion of a left ventricle contrast medium image has lower densities than a peripheral portion. However, the present invention is not limited to such a relationship between densities. If, for example, the densities of the pixels of the left ventricle portion are higher than those of a peripheral portion, the densities of the left ventricle portion may be subtracted from a predetermined value in advance. With this operation, the left ventricle portion is set to have lower densities than the peripheral portion. When the present invention is to be applied to a state wherein the densities of the pixels of a left ventricle portion are higher than those of a peripheral portion, "lower density" may be read as "higher density"; and "minimum value", as "maximum value" in the description of each embodiment. In this manner, the relationship in magnitude between density values may be reversed.

An operation of outline smoothing will be explained in reference to FIGS. 23 to 24B. FIG. 23 is a flow chart showing the operation of smoothing of an outline, and FIGS. 24A and 24B are views for explaining a method of smoothing an outline.

A variable i is set to 1 (step S18a). A (i−1)th length data to (i+1)th data are successively read (steps S18b to S18d). In this case, the data is read in a form of coordinates. That is, positions of LA(i) and $BD_1(i)$ are represented by $(x_L, Y_L)$ and $(x_B, Y_B)$, respectively (shown in FIG. 24A). A length data is obtained by following equation based on the coordinates of outline point. For example, the length of ith data is calculated by $$f_1(i)=|x_B-x_L|/\cos\theta$$

or $$f_1(i)=\{(x_L-x_B)^2+(Y_L-Y_B)^2\}^{1/2}.$$

A mean value $f_{s1}(i)$ of (i−1)th data to (i+1)th data is calculated by the following equation.

$$f_{s1}(i)=\{f_1(i-1)+f_1(i)+f_1(i+1)\}/3.$$

$f_{s1}(i)$ is temporarily stored in a memory (not shown) (step S18f).

The variable i is incremented (step S18g).

If the variable i is exceed $i_{max}$ (end data), smoothing is completed (step S18h). If not so in step S18h, steps S18b to S18g are repeated. FIG. 24B shows the result of outline smoothing.

As described above, the outline smoothing is completed, and the desired portion having smoothed outline can be obtained.

FIG. 23 shows the schematic arrangement of an X-ray diagnosing apparatus including an image processing apparatus according to the sixth embodiment of the present invention. The same reference numerals in FIG. 23 denote the same parts as in FIG. 1, and a detailed description thereof will be omitted. The apparatus of the sixth embodiment is different from that shown in FIG. 1 in that an outline extractor 3c includes a profile synthesizing section $3c_1$ and an outline determining section $3c_2$.

The profile synthesizing section $3c_1$ reads an image of a desired frame from a motion picture constituted by images of a plurality of frames recorded on an image memory 3b, and performs processing (to be described later). Thereafter, the profile synthesizing section $3c_1$ synthesizes a density profile at a position designated by the outline determining section $3c_2$ and supplies it to the outline determining section $3c_2$.

The outline determining section $3c_2$ incorporates a computer and can execute outline extraction processing (to be described later).

Figure 26:
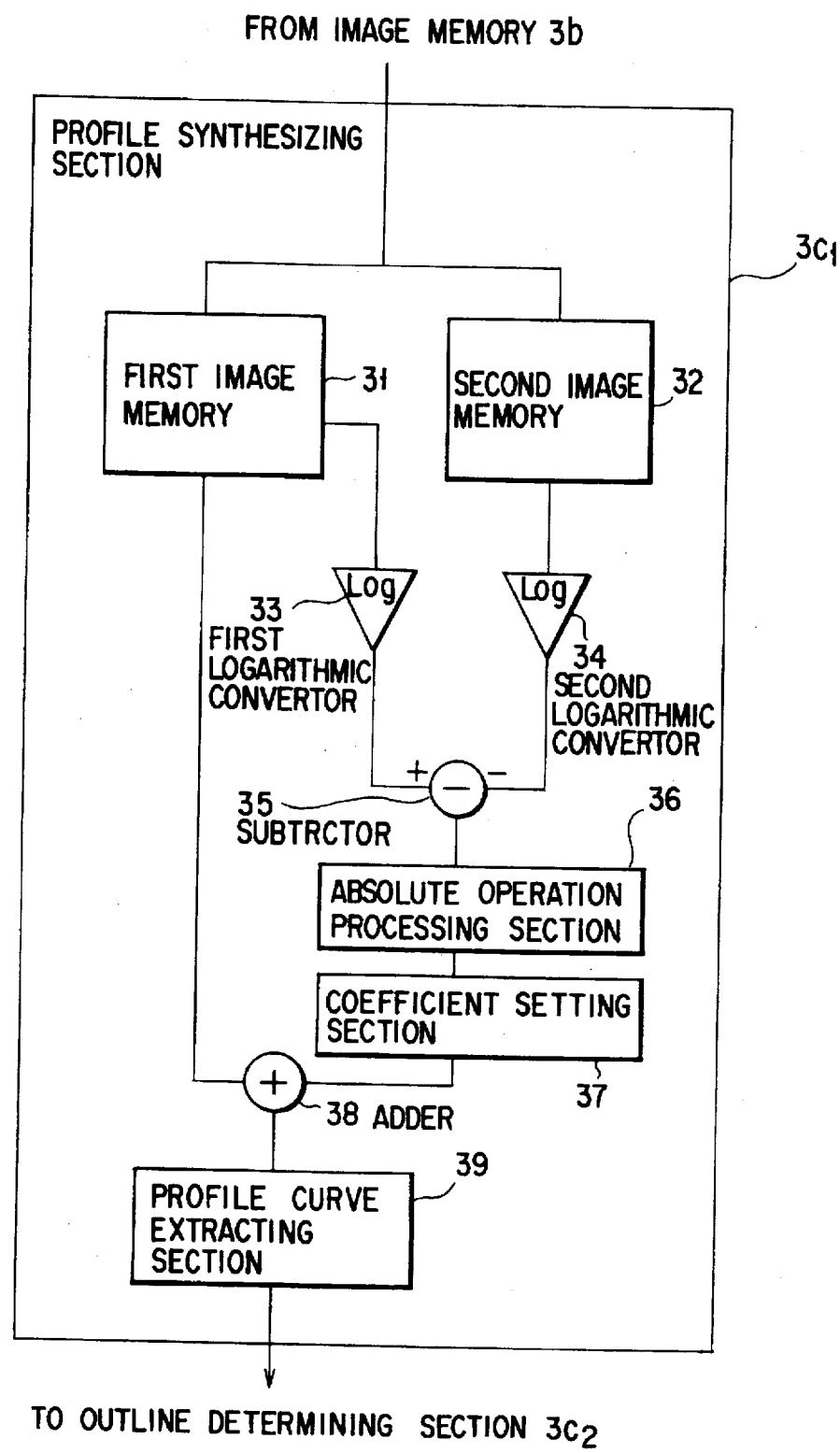
FIG. 26 is a block diagram showing the schematic arrangement of a profile synthesizing section $3c_1$.

FIG. 26 shows the schematic arrangement of the profile synthesizing section $3c_1$.

The profile synthesizing section $3c_1$ includes a first image memory 31, a second image memory 32, a first logarithmic convertor 33, a second logarithmic convertor 34, a subtracter 35, an absolute operation processing section 36, a coefficient setting section 37, an adder 38, and a profile curve extracting section 39.

The profile synthesizing section $3c_1$ selects an image at the end of diastole (to be referred to as a first ED image (end diastolic image) hereinafter) from the image memory 3b and loads it into the first image memory 31. The operator selects this image while watching images displayed on an image display section. Subsequently, the profile synthesizing section $3c_1$ loads an ED image (to be referred to as a second ED image hereinafter) one frame ahead of the selected image into the second image memory 32. The first and second ED images loaded into the first and second image memories 31 and 32 are preferably filtered by a smoothing (low-pass) filter to reduce coarseness due to X-ray noise.

Subsequently, the first and second ED images are logarithmically converted (LOG conversion) by the first and second logarithmic convertors 33 and 34, respectively, and differences between the first and second ED images, which have undergone logarithmic conversion, are obtained by the subtracter 35 in units of pixels, thereby obtaining a subtraction image. In this subtraction image, an area located near the mitral valve, in which the concentration of a contrast medium is low, exhibits negative values; a portion corresponding to the expanded ventricle of the heart exhibits positive values; and an area where the rib, the diaphragm, or the like other than the ventricle of the heart appears exhibits 0. That is, an image formed by extracting only changes in the contrast medium can be obtained.

The absolute operation processing section 36 performs absolute value processing with respect to the obtained subtraction image. More specifically, by this absolute value processing, the positive pixel values of the pixels of the area where the ventricle of the heart near the outline of the heart is expanded are kept unchanged, and the negative pixel values of the pixels of the area near the mitral valve, in which the concentration of the contrast medium is low, are converted into positive values upon inversion of the sign.

The coefficient setting section 37 sets a coefficient for adjusting each pixel value of the subtraction image which has undergone absolute value processing, multiplies the obtained subtraction image by the set coefficient, and outputs the resultant image to the adder 38.

The adder 38 adds the first ED image and the image obtained by multiplying the subtraction image by a predetermined coefficient. In an X-ray contrast medium image, a contrast medium signal appears in the direction in which the pixel value decreases. Therefore, when the absolute-value-processed image, in which a changing component of the contrast medium has a positive value, is subtracted from the first ED image, an image in which a contrast medium signal is emphasized by a changing component of the contrast medium can be obtained. Even if the coefficient setting section 37 sets a negative coefficient, and the first ED image and the subtraction image are added together, the same effect as that described above can be obtained.

The profile curve extracting section 39 reads the densities of the pixels on a straight line (i.e., the long axis) designated by the outline determining section $3c_2$ and supplies them, as a density profile, to the outline determining section $3c_2$.

Since the operation of the outline determining section $3c_2$ is the same as that in step S13 and the 10 subsequent steps in FIG. 11, an illustration and description thereof will be omitted.

The operation of the profile synthesizing section $3c_1$ having the above arrangement will be described below with reference to FIGS. 27A to 27G. FIGS. 27B to 27F respectively show an A–A' profile in FIG. 27A which is obtained by the profile synthesizing section $3c_1$.

Figure 27:
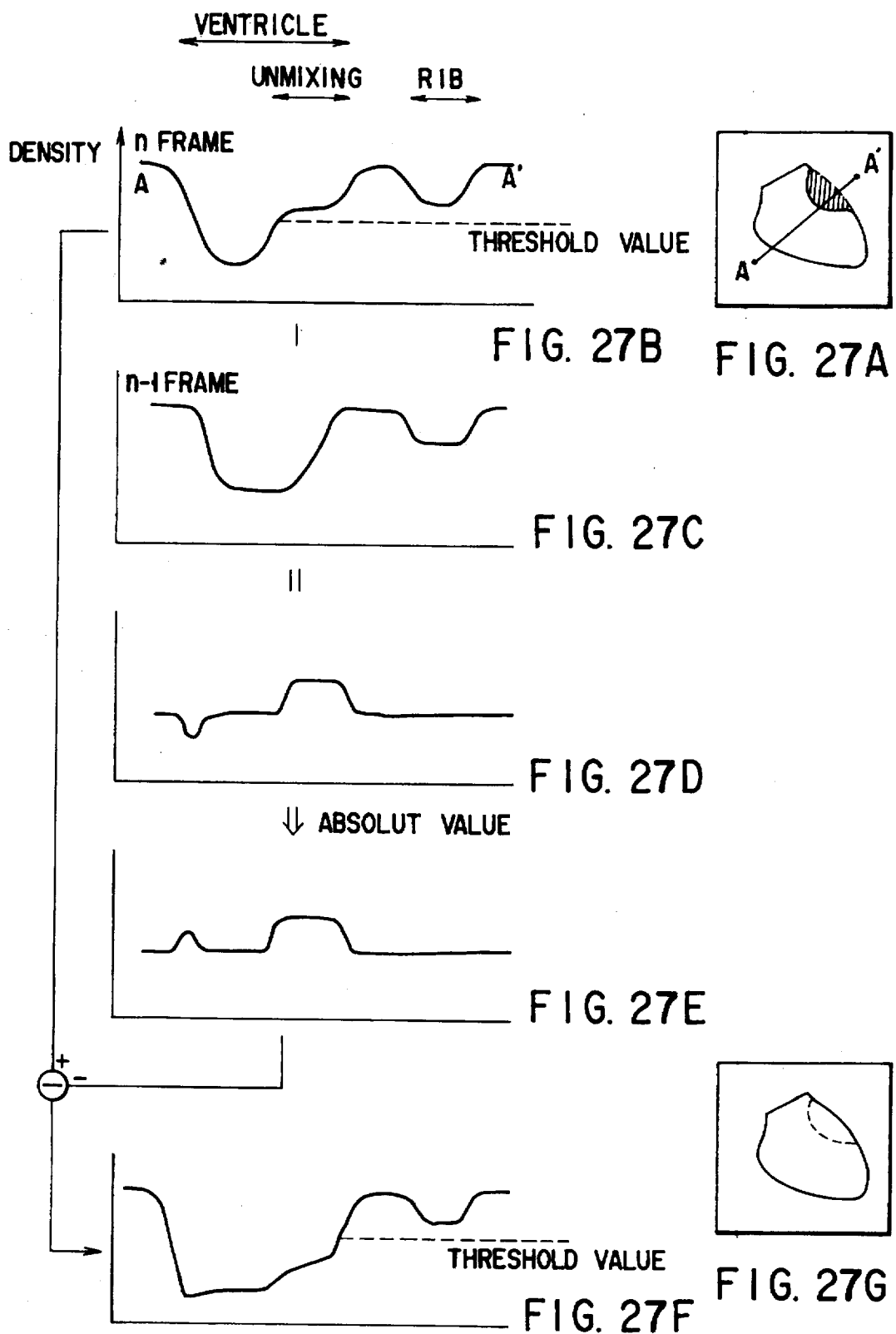
FIGS. 27A to 27G are views for explaining the operation of the profile synthesizing section $3c_1$.

Assume that the image obtained first is like the one shown in FIG. 27A. In this case, since the hatched portion has pixel values larger than a threshold value, this portion is not regarded as part of the left ventricle of the heart. As a result, an image having an omission is obtained.

The profile synthesizing section $3c_1$ loads image data from the image memory 3b. In this case, the first image memory 31 stores the first ED image having a profile like the one shown in FIG. 27B, and the second image memory 32 stores the second ED image having a profile like the one shown in FIG. 27C.

The first and second ED images are logarithmically converted by the first and second logarithmic convertors 33 and 34, respectively, and are subtracted from each other to obtain a subtraction image. FIG. 27D shows an A–A' profile obtained in this case. By performing absolute value processing of the image shown in FIG. 27D, the image shown in FIG. 27E is obtained.

Finally, the adder 38 performs emphasis processing of the image shown in FIG. 27E and adds the resultant image to the first ED image shown in FIG. 27B, thereby obtaining an image having no omission like the one shown in FIG. 27G.

According to this embodiment, therefore, even with variations in the density of a contrast medium, an accurate outline can be extracted.

Figure 28:
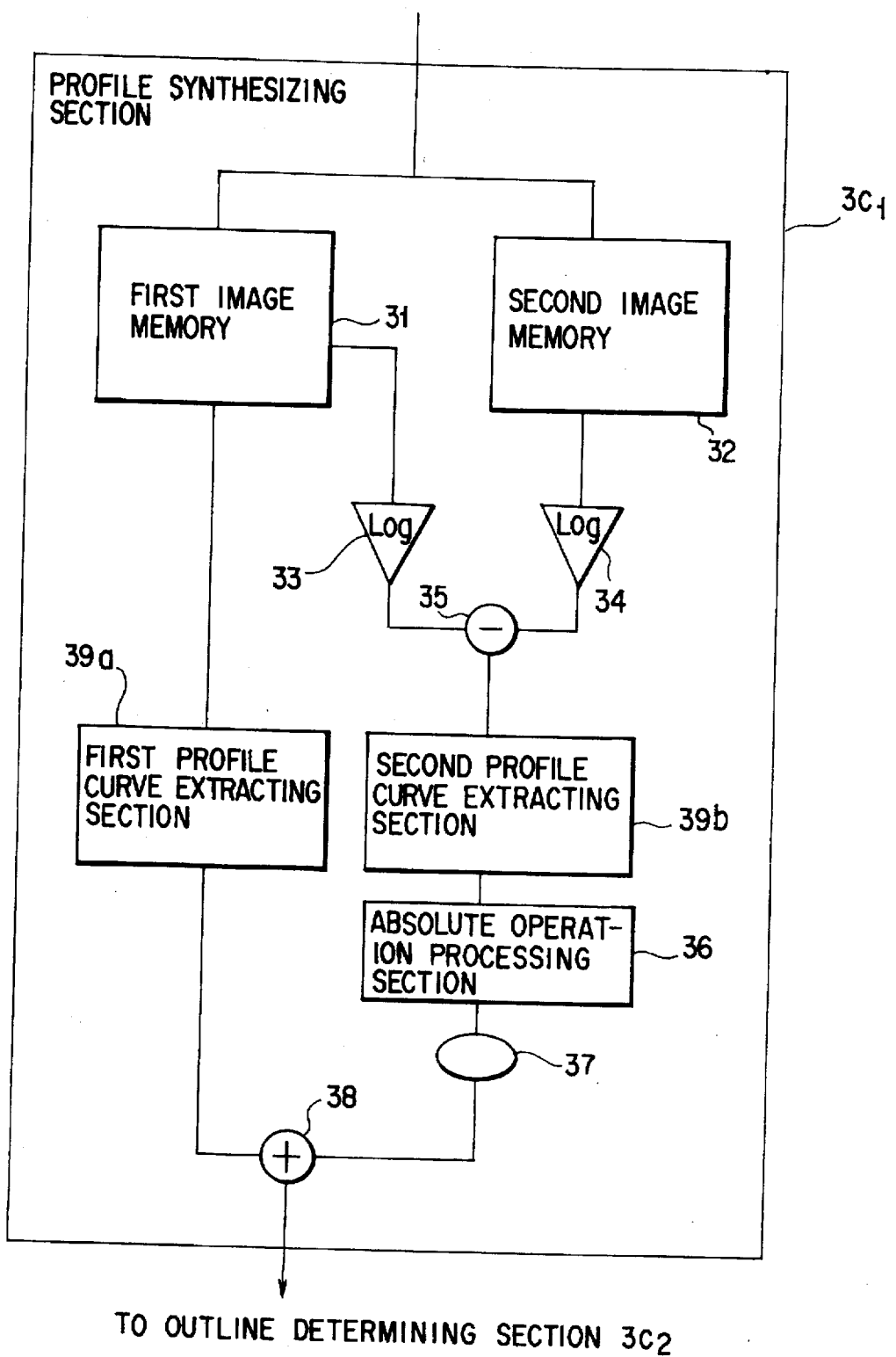
FIG. 28 is a block diagram showing the first modification of the profile synthesizing section $3c_1$.

FIG. 28 shows the first modification of the profile synthesizing section $3c_1$. The same reference numerals in FIG. 28 denote the same parts as in FIG. 26, and a detailed description thereof will be omitted.

In the first modification, the profile curve extracting section 39 is not arranged after the adder 38, but a first profile curve extracting section 39a is connected to the output of a first memory, and a second profile curve extracting section 39b is connected to the output of a subtracter 35.

After first and second ED images are input, and a subtraction image 36 is formed, a profile curve at a position designated by an outline determining section $3c_2$ is extracted from the first ED image and the subtraction image. An absolute operation processing section 36 performs absolute value processing with respect to the profile curve extracted from the subtraction image. A coefficient setting section 37 multiplies the profile, which has undergone absolute value processing, by a predetermined coefficient. An adder 38 adds the profile curve extracted from the first ED image to an output from the coefficient setting section 37. The profile curve obtained by this addition is supplied to the outline determining section $3c_2$.

With the first modification, the same profile curve as that obtained after the formation of an emphasized image can be obtained. In the first modification, since no area for the formation of an emphasized image is required, the arrangement can be simplified as compared with the embodiment shown in FIG. 26.

Figure 29:
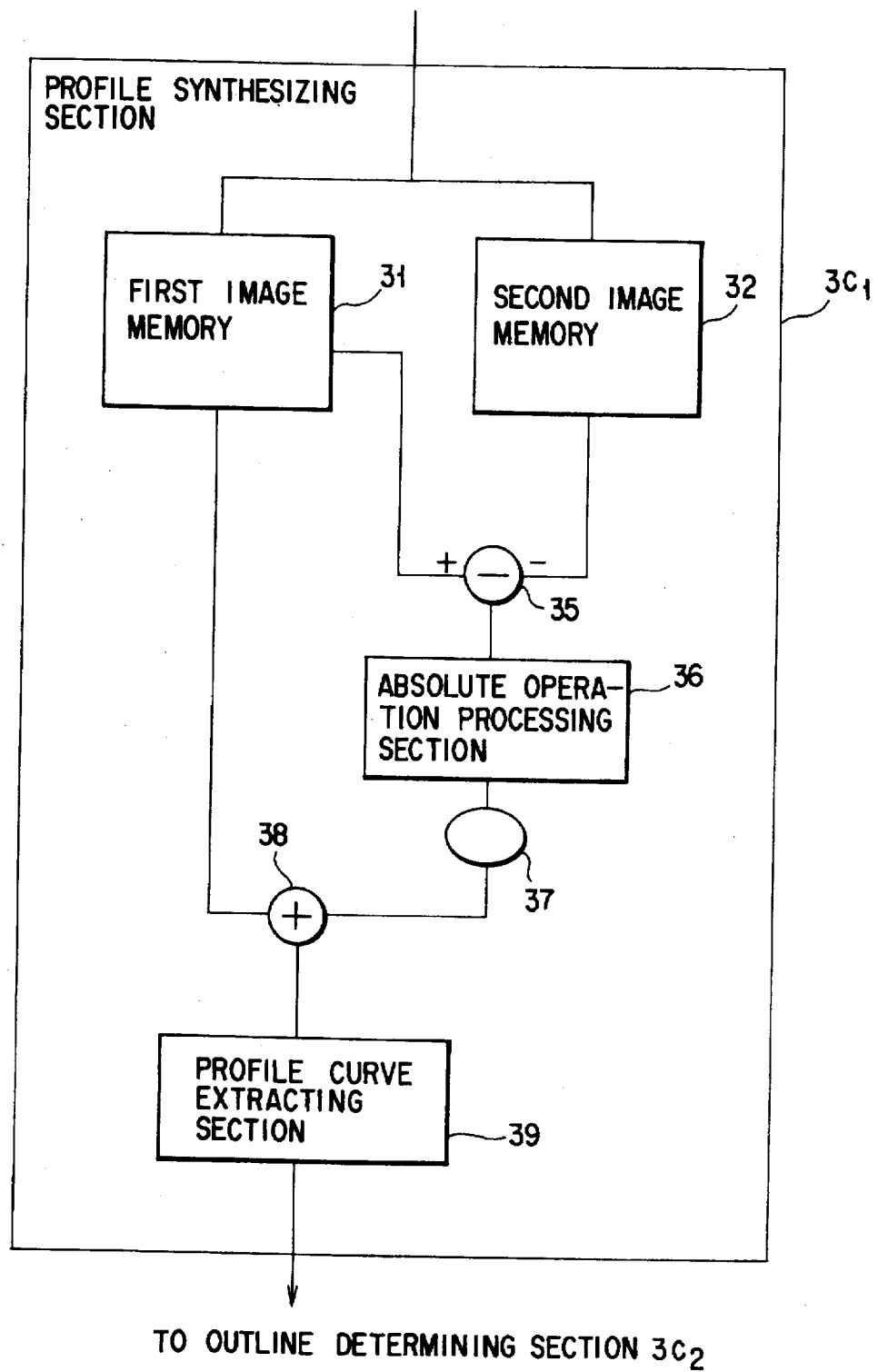
FIG. 29 is a block diagram showing the second modification of the profile synthesizing section $3c_1$.

FIG. 29 shows the second modification of the profile synthesizing section $3c_1$. The same reference numerals in FIG. 29 denote the same parts as in FIG. 26, and a detailed description thereof will be omitted.

The arrangement of the second modification is different from the arrangement shown in FIG. 26 in that the first and second logarithmic convertors 33 and 34 are omitted.

If a left ventricle contrast medium image produced as a motion picture is superposed on a portion (e.g., a rib) which absorbs a large amount of X-rays, changes in the concentration of a contrast medium at a portion where the contrast medium image is superposed on the rib or the like cannot be emphasized. For this reason, it is preferable that an emphasized image be formed by using an image obtained by performing logarithmic conversion and subtraction, as shown in FIG. 26. If, however, the left ventricle contrast medium image is not superposed on a portion which absorbs a large amount of X-rays, an image having an emphasized line segment based on changes in the concentration of the contrast medium can be obtained by the processing of the second modification. In this modification, no logarithmic conversion processing section is required, and the arrangement is simplified as compared with the embodiment shown in FIG. 26.

FIG. 30 shows the third modification of the profile synthesizing section $3c_1$. The same reference numerals in FIG. 30 denote the same parts as in FIG. 28, and a detailed description thereof will be omitted. The arrangement of the third modification is different from the arrangement shown in FIG. 28 in that the first and second logarithmic convertors 33 and 34 are omitted.

With the third modification, the same profile curve as that formed after the formation of an emphasized image can be obtained. In the third modification, no area for the formation of an emphasized image is required, and the arrangement is simplified as compared with the embodiment shown in FIG. 29.

The present invention is not limited to the above embodiments. It is apparent that various changes and modifications of the embodiments can be made within the spirit and scope of the present invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An image processing apparatus comprising:

image acquiring means for acquiring an image including a desired portion of an object to be examined;

image memory means for temporarily storing the acquired image; and outline extracting means for extracting an area of interest from a desired portion of the object wherein said outline extracting means includes long axis setting means for setting a long axis in a first direction of the image, first profile generating means for drawing a plurality of lines on the image in a second direction perpendicular to the long axis so as to divide the image stored in said image memory means into a plurality of areas, and generating a plurality of first profile data for the respective perpendicular lines, density setting means for searching a background area outside the area of interest and an inner area inside the area of interest on the basis of the first profile data, and obtaining densities of the background area and the Inner area, threshold value determining means for determining a threshold value for each of the plurality of divided areas on the basis of a weighted mean of the densities of the background area and the inner area, and outline setting means for determining an outline point constituting a boundary between the outside and inside of the area of interest by using the threshold values determined for the respective first profile data, and connecting the outline points.

2. An apparatus according to claim 1, wherein said first profile generating means includes position detecting means for detecting a maximum density position in the first profile data between the predetermined position on the outside and the long axis, in a direction from the predetermined position on the outside to the long axis, and background area density replacing means for replacing the maximum density position detected by said position detecting means with a background area density.

3. An apparatus according to claim 2, wherein said background density replacing means includes determination means for determining whether the maximum density position is between an outline point set by the immediately preceding first profile data and the predetermined position on the outside, and means for replacing the background density with a density of the maximum density position on the basis of the determination result obtained by said determination means.

4. An apparatus according to claim 2, wherein said background density replacing means includes determination means for determining whether the maximum density position is between an outline point set by the immediately preceding first profile data and the predetermined position on the outside, and starting point changing means for changing the search starting point to the maximum density position on the basis of the determination result obtained by said determination means.

5. An apparatus according to claim 1, wherein said density setting means includes means for setting an average of a sum of currently read background densities of the first profile data and previously read background densities of the first profile data.

6. An apparatus according to claim 5, wherein said first profile generating means includes means for generating first profile data proportional in number to a length of the long axis.

7. An apparatus according to claim 1, wherein said first profile generating means includes means for generating first profile data proportional in number to a length of the long axis.

8. An apparatus according to claim 1, wherein said threshold value determining means includes means for setting first and second threshold values for left and right sides of the first profile data with respect to the long axis, and said outline setting means includes means for detecting the outline points on the basis of the first and second threshold values on the left and right sides of the long axis.

9. An apparatus according to claim 1, wherein said outline extracting means further include means for searching a background area on the first profile data.

10. An apparatus according to claim 1, wherein said first profile generating means includes means for drawing the plurality of perpendicular lines at substantially equal intervals, and search starting point setting means for setting a representative point of the background area as a search starting point at a predetermined position spaced apart by a predetermined distance from an outline point obtained from the immediately preceding first profile data.

11. An apparatus according to claim 10, wherein said search starting point determining means includes means for setting a point spaced apart outward from the outline point by a distance proportional to a length of the long axis as a search starting point.

12. An image processing method comprising:

the first step of acquiring an image including a desired portion of an object to be examined;

the second step of temporarily storing the acquired image; and the third step of extracting an area of interest from the desired portion of the object, wherein the third step includes the substeps of setting a long axis in a first direction of the image to divide the image stored in said image memory means into a plurality of areas, drawing a plurality of perpendicular lines on the image in a second direction perpendicular to the long axis, and generating a plurality of first profile data for the respective perpendicular lines searching a background area outside the area of interest and an inner area inside the area of interest on the basis of each of the first profile data, and obtaining densities of the background area and the inner area, determining a threshold value for each of the plurality of divided areas on the basis of an average of a sum of the densities of the background area and the inner area, and determining outline points constituting a boundary between the outside and inside of the area of interest by using the threshold values determined for the respective first profile data, and connecting outline points.

\* \* \* \* \*